United States Patent [19]

Heeres

[11] 3,936,470
[45] Feb. 3, 1976

[54] 1,3-DIOXOLAN-2-YLMETHYLIMIDAZOLES

[75] Inventor: Jan Heeres, Vosselaar, Belgium

[73] Assignee: Janssen Pharmaceutica N.V., Beerse, Belgium

[22] Filed: Jan. 27, 1975

[21] Appl. No.: 544,157

[52] U.S. Cl............ 260/309; 260/340.9; 260/618 R; 260/618 D; 424/273
[51] Int. Cl.². .............. C07D 233/60; C07D 405/10
[58] Field of Search ...................... 260/309

[56]  References Cited
UNITED STATES PATENTS 3,575,999  4/1971  Godefroi et al.................... 260/309
3,717,655  2/1973  Godefroi et al.................... 260/309

Primary Examiner—Natalie Trousof
Attorney, Agent, or Firm—Salvatore R. Conte

[57] ABSTRACT

Novel 1-(2-$Ar^1$-4-$Ar^2$-1,3-dioxolan-2-ylmethyl)imidazoles, 1-[2-$Ar^1$-4-($Ar^2$-oxymethyl)-1,3-dioxolan-2-ylmethyl]imidazoles, 1-[2-$Ar^1$-4-($Ar^2$-thiomethyl)-1,3-dioxolan-2-ylmethyl]imidazoles, and 1-[2-$Ar^1$-4-($Ar^2$-ethyl)-1,3-dioxolan-2-ylmethyl]imidazoles, useful as antifungal and antibacterial agents.

6 Claims, No Drawings

1,3-DIOXOLAN-2-YLMETHYLIMIDAZOLES

PRIOR ART

In U.S. Pat. Nos. 3,575,999 and 3,717,655 are described some 1-(2-aryl-1,3-dioxolan-2-ylmethyl)imidazoles. The compounds of the present invention differ from the foregoing essentially by the presence of an aryl, aryloxymethyl, arylthiomethyl or arylethyl group in the 4-position of the dioxolane group.

DESCRIPTION OF THE INVENTION

This invention relates to novel imidazole derivatives having the formula:

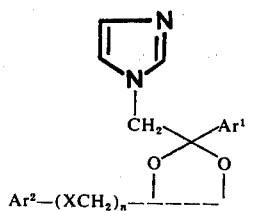
(I)

and the therapeutically acceptable acid addition salts thereof,
wherein:
Ar$^1$ is a member selected from the group consisting of phenyl, mono-, di- and trihalophenyl, loweralkylphenyl and loweralkoxyphenyl;
Ar$^2$ is a member selected from the group consisting of phenyl, substituted phenyl, naphthyl and halonaphthyl, and wherein substituted phenyl has the meaning of a phenyl group, having thereon from 1 to 3 substituents independently selected from the group consisting of halo, loweralkyl, loweralkoxy, cyano, phenyl and benzyl;
X is a member selected from the group consisting of O, S and CH$_2$; and
n is the integer 0 or 1.

As used herein, "loweralkyl" and "loweralkoxy" may be straight or branch chained and have from 1 to 6 carbon atoms, such as, for example, methyl, ethyl, propyl, butyl, tert. butyl, pentyl, hexyl and the like alkyls, and, respectively, the corresponding alkoxys such as methoxy, ethoxy, propoxy, isopropoxy, etc. The preferred loweralkyl and loweralkoxy are methyl and methoxy, respectively. The term "halo" refers to halogens of atomic weight less than 127, i.e., fluoro, chloro, bromo and iodo.

The compounds of formula (I) are conveniently prepared by reacting imidazole (II) with an appropriate reactive ester of formula (III) wherein Ar$^1$, Ar$^2$, X and n are as previously defined and wherein W is a reactive ester function, such as, halo, tosylate, mesylate and the like.

Preferred reactive esters are halides and more particularly bromides and chlorides.

In one method of conducting the reaction between imidazole and (III), imidazole is first transformed into a metal salt thereof by treatment with an appropriate metallating agent, such as, a metal alkoxide, e.g., sodium- or potassium methanolate, or a metal hydride, such as sodiumhydride. The thus-obtained salt is then reacted with (III) in an appropriate organic solvent, such as dimethylformamide or dimethylacetamide. A small amount of a metal iodide, such as sodium or potassium iodide may be added to promote the reaction.

Alternatively, the reaction of imidazole with the reactive ester (III) may also be carried out without previous salt formation, by bringing the reactants into contact with each other in an appropriate organic solvent, such as, for example, dimethylformamide or dimethylacetamide. In these circumstances it is appropriate to use an excess of imidazole or to add to the reaction mixture an appropriate base, such as sodium or potassium carbonate or bicarbonate. The use of an excessive amount of imidazole is however preferred. Further it is advantageous to conduct the reaction in the presence of a metal iodide, such as, for example, sodium or potassium iodide.

In each of the above procedures, somewhat elevated temperatures may be employed to enhance the rate of the reaction and most conveniently the reactions are carried out at the reflux temperature of the reaction mixture.

The final product may be further purified by common purification procedures, such as extraction, trituration, crystallization, chromatography, etc.

The foregoing procedures are more fully illustrated by the following schematic representation.

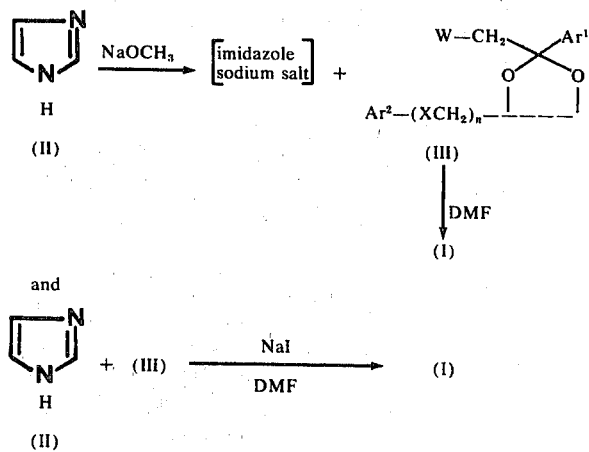

The imidazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydriodic acid; sulfuric, nitric or thiocyanic acid; a phosphoric acid; an organic acid such as acetic, propionic, glycolic, lactic, pyruvic, oxalic, malonic, succinic, maleic, fumaric, malic, tartaric, citric, benzoic, cinnamic, mandelic, methanesulfonic ethanesulfonic, hydroxyethanesulfonic, p-toluenesulfonic, salicylic, p-aminosalicylic, 2-phenoxybenzoic or 2-acetoxybenzoic acid. The salts are in turn converted to the corresponding free bases in the usual manner, e.g., by reaction with alkali such as sodium or potassium hydroxide.

The intermediates of formula (III) wherein n is 1 and $Ar^1$ and $Ar^2$ have the above indicated meanings, and those wherein n is zero and wherein at least one of the aryls $Ar^1$ and $Ar^2$ is a substituted phenyl as previously defined, and those wherein $Ar^2$ is naphthyl or halonaphthyl, are deemed to be novel and, as useful intermediates for the preparation of the desired compounds of formula (I), they constitute an additional feature of this invention.

The intermediates of formula (III) may be prepared by methods analogous to that described for the preparation of 2-bromomethyl-2,4-diphenyl-1,3-dioxolane [Synthesis, 1974, (1), 23]. Such methods consist in a ketalisation of an appropriate arylketone of formula (IV) wherein $Ar^1$ and W have the indicated meaning with an appropriate glycol of formula (V) wherein $Ar^2$, X and n are as previously defined. In a preferred method both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as para-toluenesulfonic acid. Suitable organic solvents are for example, aromatic hydrocarbons, such as benzene, toluene, xylene and the like and saturated hydrocarbons, such as cyclohexane.

After the reaction is completed, the dioxolane derivative (III) is further purified by conventional means. The foregoing reactions are illustrated in the following schematic representation:

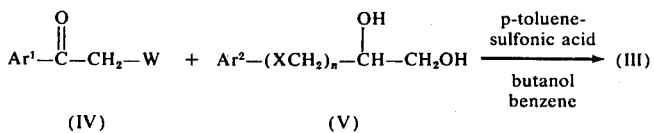

Alternatively the intermediates of formula (III) are conveniently prepared by transketalization of a ketal derivative of a ketone of formula (IV) such as for example, a lower alkyl ketal or a cyclic lower alkylene ketal, with a glycol of formula (V) under conditions similar to those described hereinbefore for the direct ketalization The lower alkyl ketals and cyclic lower alkylene ketals used herein as starting materials are easily obtained by ketalization of a ketone of formula (IV) with a lower alkanol or alkanediol according to methodologies known in the art. A number of such compounds and methods of preparing the same are described in U.S. Pat. Nos. 3,575,999 and 3,717,655.

The precursor arylketones of formula (IV) are generally known and may be prepared according to known methods as described in the literature.

The precursor glycols of formula (V) wherein n is 0, and those wherein n is 1 and X is O or S are also generally known and their preparation may be carried out according to known procedures.

A number of the precursor glycols of formula (V) wherein X is $CH_2$ and n is 1, (V-a), are also known and methods of preparation described therefor in the literature are generally applicable to synthesize the compounds (V-a).

An alternative and convenient method of preparing them is by the following sequence of reactions.

A halide of formula (VI) is converted into a Grignard complex thereof in the usual manner and the thus-obtained Grignard complex is reacted with a 2-(halomethyl)oxirane of formula (VII) to obtain a α-(halomethyl)alcohol compound of formula (VIII). The compound (VIII) is subsequently converted into an oxirane derivative of formula (IX) by treatment with alkali, e.g., with sodium hydroxide in an appropriate solvent, such as, for example, 2,2'-oxybispropane. The oxirane derivative (IX) is then treated with an appropriate acid, such as, for example, oxalic, hydrochloric acid, etc. to obtain the desired glycol of formula (V-a).

The foregoing sequence of reactions is more fully illustrated in the following schematic representation.

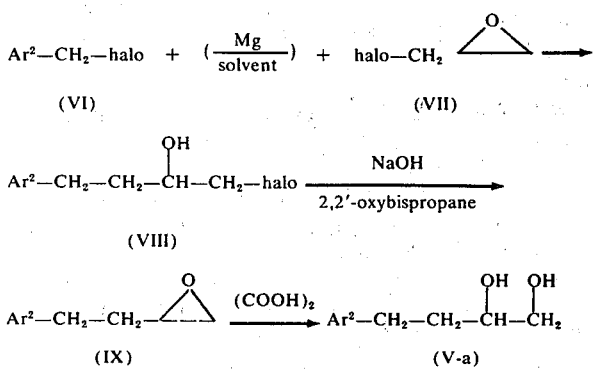

From formula (I) it is evident that the compounds (I) of this invention have two asymmetric carbon atoms in their structure and consequently they exist under different stereochemical optical isomeric forms. The stereochemical optical isomeric forms of (I) and the therapeutically active acid addition salts thereof are intended to be within the scope of this invention.

The diastereoisomeric racemates of (I), denoted as cis (+) and trans (+) according to the rules described in "Naming and Indexing of Chemical Substances for Chemical Abstracts during the 9th. Collective Period (1972 – 1976)" published in C.A. 1972, 76, Index Guide Section IV, p, 85, may be obtained separately by conventional methods. One such method is, for example, selective crystallization whereby one of the two forms precipitates and the other remains in the solution, wherefrom the latter may be isolated, for example, by evaporating the solvent. For a number of compounds the stereochemical configuration was experimentally determined. In the remaining cases it is conventionally agreed to designate the first precipitating form as A and the remaining as B, without further reference to the actual stereochemical configuration.

Since the asymmetric carbon atoms are already present in the intermediates (III) it is also possible to separate cis- and trans-forms, or generally A and B forms at this stage, whereupon the corresponding form of (I) may be obtained after reaction of one of the foregoing with imidazole as previously described. The separation of cis- and trans-forms of (III) may be performed by selective crystallization as indicated hereinbefore.

The diastereoisomeric racemates cis (+) and trans (+) may be further resolved into their optical isomers cis (+), cis (−), trans (+) and trans (−) by methods known to those skilled in the art.

The subject compounds of formula (I) and the acid addition salts thereof are useful against in combating fungi and bacteria as demonstrated by their broad spectrum of antifungal or antibacterial action. The data given in the following tables illustrates such activity. The compounds in the tables are not listed for purposes of limiting the invention thereto, but only in order to exemplify the useful properties of all the compounds within the scope of formula (I).

The test for antifungal activity was performed using Sabouraud's liquid medium in test tubes each containing 4.5 ml of liquid medium, autoclave at 120°C for 15 minutes.

The substances were dissolved in 50% ethanol at a concentration of 20 mg/ml and subsequently diluted with sterile distilled water to a concentration of 10 mg/ml. Successive decimal dilutions were then made with distilled water to give a series of stock solutions. To each tube containing 4.5 ml of Sabouraud's liquid medium was added 0.5 ml of one of the stock solutions to give a concentration of the drug under investigation of 100 μg, 10 μg, 1 μg or 0.1 μg per ml of medium.

Filamentous fungi were incubated at 25°C for 2 – 3 weeks. A square block of side 2 mm. was excised and inoculated into the liquid medium. A three-day old culture on Sabouraud's liquid medium was used for yeasts, and the inoculum was 0.05 ml per tube.

All the cultures were incubated at 25°C for 14 days. The final readings were taken after two weeks and are summarized in the Tables A as follows:

++++ = complete inhibition of growth at 0.1 μg/ml
+++ = complete inhibition of growth at 1 μg/ml
++ = complete inhibition of growth at 10 μg/ml
+ = complete inhibition of growth at 100 μg/ml
0 = no effect, i.e. growth was observed at the highest concentration tested (100 μg/ml). In a first screening the drugs under investigation were tested against the following 11 fungi:

1. Microsporum canis (M.c. in the tables)
2. Ctenomyces mentagrophytes (Ct. m. in the tables)
3. Trichophyton rubrum (Tr. r. in the tables)
4. Phialophora verrucosa (Ph. v. in the tables)
5. Cryptococcus neoformans (Cr. n. in the tables)
6. Candida tropicalis (C. tr. in the tables)
7. Candida albicans (C. alb. in the tables)
8. Mucor species (Muc. in the tables)
9. Aspergillus fumigatus (A.f. in the tables)
10. Sporotrichum schenckii (Sp. s. in the tables)
11. Saprolegnia species (Sap. in the tables)

All the substances showing activity against the Phycomycetes Mucor at the 10 μg/ml concentration were also tested against four other species of phycomycetes, namely:

1. Absidia ramosa (Abs. r. in the tables)
2. Basidiobolus meristosporus (Bas. m. in the tables)
3. Mortierella species (Mort. in the tables)
4. Rhizopus (Rhi in the tables).

The method used in this section screen was exactly the same as described above, and the results are given in Tables B.

Bactericidal tests were performed on cultures on phenol red dextrose broth Difco medium. The same decimal dilution techniques as described herebefore were used. The inoculum consisted of a platinum loop (5 mm diameter) from a 24 hour broth culture.

48 hours after incubation, subcultures were made from each culture and for the assessment of the bactericidal activity of the drugs under investigation the presence or absence of growth after 7 days incubation was scored as described above.

The substances were tested against the following gram-negative bacilli:

1. Salmonella pullorum gallinarum (SPG in the table)
2. Escherichia coli (E. coli in the table), and
3. Pseudomonas aeruginosa (ps. aer. in the table)

and against the following gram-positive bacilli and cocci:

1. Erysipelothrix insidioda (E. ins. in the table)
2. Staphylococcus hemolyticus (Staph. in the table), and
3. Streptococcus pyogenes (Strept. in the table).

The results are summarized in Tables C.

Tables A

ANTIFUNGAL ACTIVITY

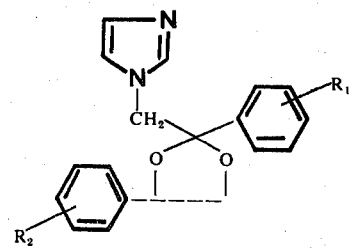

ANTIFUNGAL ACTIVITY

| $R_1$ | $R_2$ | M. c. (1) | Ct. m. (2) | Tr. r. (3) | Ph. v. (4) | Cr. n. (5) | C. tr. (6) | C. alb. (7) | Muc. (8) | A. f. (9) | Sp. s. (10) | Sap. (11) |
|---|---|---|---|---|---|---|---|---|---|---|---|---|
| 4-Cl | 4-Cl | ++++ | ++++ | ++++ | + | +++ | ++ | + | +++ | +++ | ++ | ++ |
| 4-Cl | H | ++ | +++ | +++ | + | ++ | 0 | + | + | ++ | ++ | + |
| 4-Cl | 2,4-(Cl)$_2$ | ++ | +++ | +++ | + | ++ | 0 | + | + | + | ++ | + |
| 4-Br | 4-Cl | +++ | +++ | +++ | + | + | + | 0 | 0 | ++ | ++ | + |
| 4-Br | 2,4-(Cl)$_2$ | ++ | ++ | +++ | 0 | 0 | 0 | 0 | + | 0 | + | 0 |

Tables A-continued

1
ANTIFUNGAL ACTIVITY

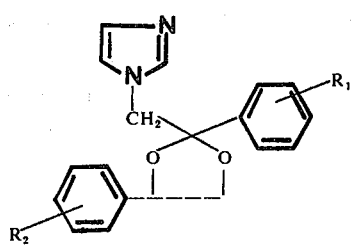

ANTIFUNGAL ACTIVITY

| $R_1$ | $R_2$ | M. c. (1) | Ct. m. (2) | Tr. r. (3) | Ph. v. (4) | Cr. n. (5) | C. tr. (6) | C. alb. (7) | Muc. (8) | A. f. (9) | Sp. s. (10) | Sap. (11) |
|---|---|---|---|---|---|---|---|---|---|---|---|---|
| 2,4-(Cl)$_2$ | H | +++ | +++ | +++ | + | + | 0 | + | + | +++ | ++ | + |
| 4-OCH$_3$ | 4-Cl | +++ | +++ | ++ | + | 0 | 0 | 0 | + | +++ | ++ | + |
| H | 2,4-(Cl)$_2$ | ++ | +++ | +++ | + | ++ | 0 | 0 | + | ++ | ++ | + |
| 2,4-(Cl)$_2$ | 4-Cl | +++ | +++ | +++ | + | +++ | ++ | + | +++ | +++ | ++ | + |
| H | 4-Cl | +++ | +++ | +++ | + | ++ | + | 0 | + | ++ | ++ | + |
| 4-Cl | 2-Cl | ++ | +++ | +++ | + | ++ | 0 | 0 | + | + | +++ | ++ |
| 2-Cl | 2,4-(Cl)$_2$ | +++ | +++ | +++ | + | +++ | 0 | 0 | 0 | +++ | +++ | ++ |
| 4-Br | 2-Cl | +++ | +++ | +++ | + | +++ | 0 | + | ++ | + | ++ | + |
| 2-Cl | 4-Cl | +++ | +++ | +++ | + | + | + | + | + | +++ | ++ | + |
| 2,4-(Cl)$_2$ | 2,4-(Cl)$_2$ | ++ | +++ | +++ | + | +++ | 0 | 0 | + | +++ | ++ | + |
| 4-Br | H | +++ | +++ | +++ | + | ++ | 0 | + | + | + | + | + |
| H | 4-Br | +++ | +++ | +++ | + | ++ | 0 | 0 | + | ++ | ++ | + |
| 4-CH$_3$ | 2,4-(Cl)$_2$ | ++ | +++ | +++ | + | +++ | 0 | 0 | + | + | ++ | + |
| 4-Br | 4-Br | +++ | +++ | +++ | + | +++ | + | 0 | ++ | +++ | ++ | + |
| 2,4-(Cl)$_2$ | 2-Cl | ++ | +++ | +++ | + | +++ | + | + | + | + | ++ | + |
| 4-CH$_3$ | 4-Cl | +++ | +++ | +++ | + | +++ | + | 0 | ++ | +++ | ++ | + |
| 2,4-(Cl)$_2$ | 4-Br | +++ | +++ | +++ | + | +++ | ++ | + | +++ | +++ | ++ | + |
| 4-Cl | 4-Br | +++ | +++ | +++ | + | +++ | ++ | ++ | ++ | +++ | ++ | +++ |
| 4-CH$_3$ | 4-Br | +++ | +++ | +++ | 0 | 0 | 0 | 0 | 0 | +++ | 0 | ++ |
| 3-Cl | 2,4-(Cl)$_2$ | + | ++ | +++ | 0 | + | 0 | 0 | + | + | ++ | + |
| 2-Cl | 4-Br | +++ | +++ | +++ | ++ | +++ | ++ | + | ++ | +++ | ++ | ++ |
| 4-CH$_3$ | 2-Cl | ++ | +++ | +++ | + | + | 0 | 0 | + | + | ++ | + |
| 4-Cl | 4-CH$_3$ | +++ | +++ | +++ | + | +++ | 0 | + | + | +++ | ++ | + |
| 4-Br | 4-CH$_3$ | +++ | ++ | +++ | + | ++ | 0 | ++ | ++ | +++ | ++ | + |
| 4-Cl | 4-F | +++ | +++ | +++ | + | ++ | + | + | ++ | +++ | ++ | + |
| 4-Br | 4-F | +++ | +++ | +++ | + | ++ | + | + | +++ | +++ | ++ | + |

Tables A

2
ANTIFUNGAL ACTIVITY

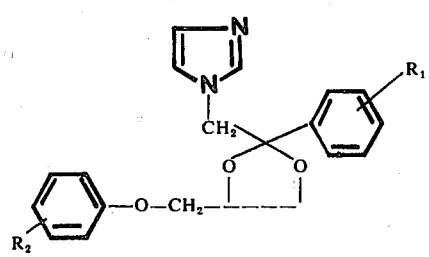

ANTIFUNGAL ACTIVITY

| $R_1$ | $R_2$ | Isomer | M.c. (1) | Ct.m. (2) | Tr.r. (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|---|
| 4-Cl | 2-CH$_3$,4-Cl | cis | 0 | ++ | ++ | 0 | + | 0 | 0 | 0 | 0 | 0 | 0 |
| 4-Cl | 4-CH$_3$ | trans | ++ | ++++ | +++ | ++ | +++ | 0 | + | + | ++ | ++ | ++ |
| 4-Cl | 2-CH$_3$,4-Cl | trans | + | +++ | +++ | 0 | ++ | 0 | 0 | ++ | + | ++ | + |
| 4-Cl | 4-CH$_3$ | cis | +++ | ++++ | ++++ | ++ | +++ | 0 | 0 | + | +++ | +++ | ++ |
| 4-Cl | 4-Cl | A | +++ | ++++ | ++++ | 0 | ++ | 0 | 0 | + | +++ | 0 | + |
| 4-Cl | 4-Cl | B | ++ | ++++ | +++ | + | + | 0 | 0 | ++ | ++ | ++ | ++ |
| 4-Cl | 4-F | cis | +++ | ++++ | +++ | + | + | 0 | 0 | ++ | ++ | ++ | ++ |
| 4-Cl | 2-CH$_3$ | A | ++ | +++ | +++ | + | ++ | 0 | 0 | + | ++ | ++ | + |
| 4-Cl | 2-Cl | A | 0 | +++ | +++ | 0 | ++++ | 0 | 0 | 0 | 0 | 0 | 0 |
| 4-Cl | 2-CH$_3$ | B | ++ | ++++ | ++++ | + | ++ | 0 | + | 0 | ++ | ++ | + |
| 4-Cl | 2,4-(Cl)$_2$ | B | ++ | ++++ | +++ | 0 | ++ | 0 | 0 | ++ | ++ | ++ | + |
| 4-Cl | 4-OCH$_3$ | A | +++ | ++++ | ++++ | + | +++ | 0 | 0 | 0 | ++ | ++ | ++ |
| 4-Cl | 4-F | trans | ++ | ++++ | +++ | + | ++ | 0 | 0 | + | + | + | ++ |
| 4-Cl | 4-OCH$_3$ | B | + | ++++ | ++ | + | ++ | 0 | 0 | 0 | + | ++ | ++ |
| 4-Cl | 2,6-(Cl)$_2$ | A | + | ++++ | ++++ | 0 | ++ | 0 | 0 | ++ | ++ | ++ | + |
| 4-Cl | 2-Cl | B | ++ | +++ | ++++ | + | ++ | 0 | 0 | 0 | ++ | ++ | + |
| 4-Cl | 2,6-(Cl)$_2$ | B | ++ | ++ | +++ | + | ++ | 0 | 0 | + | ++ | + | 0 |
| 2,4-(Cl)$_2$ | 4-CH$_3$ | B | ++ | ++ | ++ | + | ++ | 0 | 0 | + | ++ | ++ | ++ |
| 2,4-(Cl)$_2$ | 4-F | A | ++ | +++ | ++ | ++ | ++ | ++ | 0 | + | ++ | ++ | ++ |
| 2,4-(Cl)$_2$ | 2-CH$_3$ | A | +++ | +++ | +++ | + | +++ | 0 | 0 | +++ | ++ | ++ | + |
| 2,4-(Cl)$_2$ | 4-CH$_3$ | A | ++ | +++ | +++ | ++ | +++ | 0 | 0 | +++ | +++ | +++ | ++ |
| 2,4-(Cl)$_2$ | 4-OCH$_3$ | A | ++++ | ++++ | +++ | ++ | ++++ | 0 | 0 | ++ | ++ | ++++ | +++ |

Tables A-continued

2. ANTIFUNGAL ACTIVITY

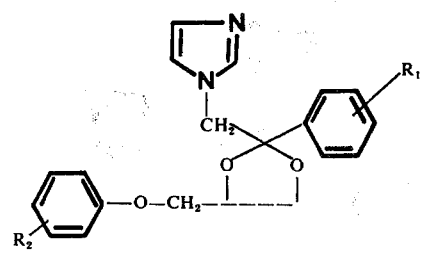

| $R_1$ | $R_2$ | Isomer | M.c. (1) | Ct.m. (2) | Tr.r. (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|---|
| 2,4-(Cl)$_2$ | 4-Cl | cis | ++++ | ++++ | ++++ | ++ | ++++ | 0 | 0 | +++ | ++ | +++ | ++ |
| 2,4-(Cl)$_2$ | 2-CH$_3$ | B | ++ | +++ | +++ | + | ++ | 0 | 0 | ++ | ++ | ++ | + |
| 2,4-(Cl)$_2$ | 2,4-(Cl)$_2$ | A | ++ | +++ | +++ | 0 | +++ | 0 | 0 | 0 | 0 | ++ | + |
| 2,4-(Cl)$_2$ | 4-Cl | trans | ++ | +++ | +++ | + | ++ | 0 | 0 | ++ | ++ | ++ | + |
| 2,4-(Cl)$_2$ | 4-Br | A | ++ | +++ | +++ | + | +++ | +++ | 0 | ++ | +++ | ++ | ++ |
| 2,4-(Cl)$_2$ | 2,4-(Cl)$_2$ | B | ++ | +++ | +++ | + | ++ | 0 | 0 | + | + | ++ | + |
| 2,4-(Cl)$_2$ | H | A | +++ | +++ | +++ | ++ | +++ | ++ | 0 | ++ | +++ | +++ | ++ |
| 2,4-(Cl)$_2$ | 3,4-(Cl)$_2$ | A | +++ | +++ | +++ | + | +++ | 0 | 0 | ++ | +++ | +++ | + |
| 2,4-(Cl)$_2$ | 3-Cl | A | +++ | +++ | +++ | + | +++ | ++ | 0 | ++ | +++ | +++ | + |
| 2,4-(Cl)$_2$ | 2-Cl | A | +++ | +++ | +++ | + | +++ | ++ | + | ++ | +++ | +++ | + |
| 2,4-(Cl)$_2$ | 2-CH$_3$,4-Cl | A + B | +++ | +++ | +++ | 0 | +++ | 0 | 0 | ++ | ++ | ++ | + |
| 2,4-(Cl)$_2$ | 2-Cl | B | ++ | +++ | +++ | 0 | ++ | 0 | 0 | 0 | + | ++ | + |
| 2,4-(Cl)$_2$ | 2,6-(Cl)$_2$ | A | ++ | +++ | +++ | + | +++ | 0 | 0 | 0 | ++ | ++ | + |
| 2,4-(Cl)$_2$ | 3,5-(CH$_3$)$_2$,4-Cl | A | 0 | 0 | ++ | 0 | 0 | 0 | 0 | 0 | 0 | 0 | 0 |
| 2,4-(Cl)$_2$ | 2,4-(Br)$_2$ | A | 0 | 0 | + | 0 | +++ | 0 | 0 | 0 | 0 | 0 | 0 |
| 2,4-(Cl)$_2$ | 4-CN | A | +++ | +++ | +++ | ++ | +++ | ++ | 0 | 0 | ++ | + | ++ |
| 2,4-(Cl)$_2$ | 2-Br | cis | ++ | +++ | +++ | 0 | +++ | 0 | 0 | +++ | ++ | ++ | + |
| 2,4-(Cl)$_2$ | 2-OCH$_3$ | A | ++ | +++ | +++ | + | +++ | + | 0 | 0 | ++ | ++ | + |
| 2,4-(Cl)$_2$ | 2-Br | trans | ++ | +++ | ++ | 0 | +++ | 0 | 0 | + | ++ | ++ | + |
| 2,4-(Cl)$_2$ | 2,4,6-(Cl)$_3$ | A | 0 | +++ | ++ | 0 | +++ | + | 0 | 0 | 0 | 0 | 0 |
| 2,4-(Cl)$_2$ | 2,5-(CH$_3$)$_2$ | A | +++ | +++ | +++ | 0 | +++ | 0 | 0 | + | ++ | ++ | + |
| 2,4-(Cl)$_2$ | 2,5-(CH$_3$)$_2$ | B | ++ | ++ | +++ | 0 | ++ | 0 | 0 | 0 | ++ | + | + |
| 2,4-(Cl)$_2$ | 2-Cl,4-tert.but. | A | 0 | + | ++++ | 0 | ++++ | 0 | 0 | 0 | 0 | 0 | 0 |
| 2,4-(Cl)$_2$ | 2,4,5-(Cl)$_3$ | A | 0 | 0 | 0 | 0 | 0 | 0 | 0 | 0 | 0 | 0 | 0 |
| 2,4-(Cl)$_2$ | 2-Cl,4-tert.but. | B | + | + | + | 0 | + | 0 | 0 | 0 | + | 0 | 0 |
| 2,4-(Cl)$_2$ | 2,4,5-(Cl)$_3$ | B | + | ++ | ++ | 0 | + | 0 | 0 | 0 | 0 | 0 | 0 |
| 2,4-(Cl)$_2$ | 2,5-(Br)$_2$,4-CH$_3$ | A | + | ++ | ++++ | 0 | ++++ | 0 | 0 | + | + | + | 0 |
| 2,4-(Cl)$_2$ | 2-F | A | ++ | ++++ | ++++ | + | ++++ | ++ | + | ++ | ++++ | ++++ | ++ |
| 4-CH$_3$ | 4-Br | A | ++++ | ++++ | ++++ | ++ | ++++ | + | 0 | 0 | ++++ | ++++ | ++ |
| 4-Cl | 4-Br | A | ++++ | ++++ | ++++ | ++ | ++++ | 0 | 0 | 0 | ++++ | ++ | + |
| 4-Br | 4-Br | A | ++++ | ++++ | ++++ | + | ++++ | 0 | 0 | 0 | + | + | ++ |
| 2,4-(Cl)$_2$ | 2-OC$_2$H$_5$ | A | ++ | ++++ | ++++ | + | ++++ | + | 0 | 0 | ++ | ++ | + |
| 2-Cl | 4-Br | A + B | ++ | ++++ | ++ | ++ | ++++ | + | + | 0 | ++ | ++ | ++ |
| 2-Cl | 4-Br | B | ++ | ++++ | ++ | + | ++++ | 0 | 0 | + | + | ++++ | + |
| H | 4-Br | A | ++ | ++++ | +++ | ++ | ++++ | 0 | 0 | 0 | ++ | ++ | ++ |
| 2-Br | 4-Br | A | ++ | ++++ | ++ | ++ | ++++ | ++ | + | ++ | ++ | ++ | + |
| 2-Br | 4-Br | B | ++ | ++++ | ++ | ++ | ++ | 0 | 0 | 0 | ++ | ++++ | + |
| 2,4-(Cl)$_2$ | 4-C$_6$H$_5$ | A + B | 0 | ++++ | ++++ | 0 | 0 | 0 | 0 | 0 | 0 | 0 | 0 |
| 2,4-(Cl)$_2$ | 4-C$_6$H$_5$ | B | 0 | 0 | 0 | 0 | 0 | 0 | 0 | 0 | 0 | 0 | 0 |
| 2,4-(Cl)$_2$ | 2,6-(CH$_3$)$_2$ | A | ++++ | ++++ | ++++ | 0 | + | + | 0 | + | ++ | + | + |
| 2,4-(Cl)$_2$ | 4-Br | B | ++ | ++++ | ++++ | 0 | 0 | 0 | 0 | ++ | + | ++++ | + |
| 2,4-(Cl)$_2$ | 2,6-(CH$_3$)$_2$ | A + B | ++ | ++++ | ++++ | 0 | 0 | 0 | 0 | + | + | ++ | 0 |
| 2,4-(Cl)$_2$ | 3,5-(CH$_3$)$_2$ | A | +++ | +++ | +++ | 0 | +++ | 0 | 0 | 0 | ++ | 0 | 0 |
| 2,4-(Cl)$_2$ | 4-iC$_3$H$_7$ | A + B | +++ | +++ | +++ | + | +++ | +++ | 0 | + | +++ | ++ | + |
| 2,4-(Cl)$_2$ | 2-Cl,6-CH$_3$ | A | +++ | +++ | +++ | + | +++ | +++ | + | +++ | +++ | +++ | + |
| 2,4-(Cl)$_2$ | 4-tert.but. | A | ++ | ++++ | ++++ | 0 | ++ | 0 | 0 | 0 | + | + | 0 |
| 2,4-(Cl)$_2$ | 3,5-(Cl)$_2$ | A | ++++ | ++++ | ++++ | 0 | 0 | 0 | 0 | ++ | ++ | 0 | 0 |
| 2,4-(Cl)$_2$ | 3-CH$_3$, 4-Cl | A | ++++ | ++++ | ++++ | + | ++++ | 0 | 0 | + | ++++ | ++ | + |

Tables A

3. ANTIFUNGAL ACTIVITY

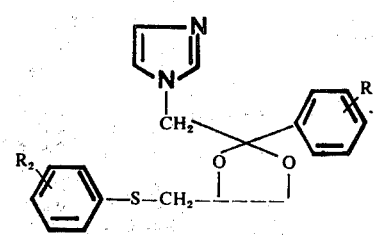

| $R_1$ | $R_2$ | Isomer | M.c. (1) | Ct.m. (2) | Tr.R. (3) | Ph.V. (4) | Cr.n. (5) | C.tr. (6) | C.alb. (7) | Muc. (8) | A.f. (9) | Sp.s (10) | Sap. (11) |
|---|---|---|---|---|---|---|---|---|---|---|---|---|---|
| 2,4-(Cl)$_2$ | 4-Br | A + B | ++++ | ++++ | ++++ | + | ++++ | ++ | + | ++ | ++ | ++++ | + |

Tables A-continued

ANTIFUNGAL ACTIVITY

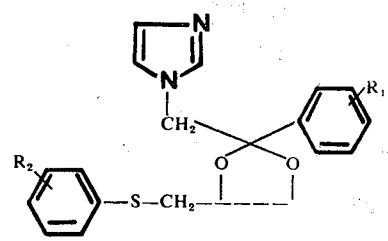

| R₁ | R₂ | Isomer | M.c. (1) | Ct.m. (2) | Tr.R. (3) | Ph.V. (4) | Cr.n. (5) | C.tr. (6) | C.alb. (7) | Muc. (8) | A.f. (9) | Sp.s (10) | Sap. (11) |
|---|---|---|---|---|---|---|---|---|---|---|---|---|---|
| 2,4-(Cl)₂ | H | A + B | ++++ | ++++ | ++++ | ++ | ++++ | ++ | + | +++ | ++ | ++++ | ++ |

Tables A

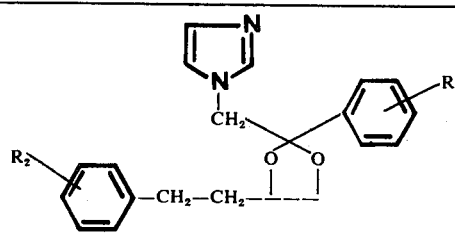

| R₁ | R₂ | Isomer | M.c. (1) | Ct.m. (2) | Tr.R. (3) | Ph.V. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|---|
| 2,4-(Cl)₂ | 2-Cl | | ++++ | ++++ | ++++ | + | ++++ | ++ | 0 | ++ | ++++ | ++ | + |
| 2,4-(Cl)₂ | 2,4-(Cl)₂ | | ++ | ++++ | ++++ | 0 | ++++ | ++ | 0 | ++ | ++ | ++ | + |
| 2,4-(Cl)₂ | 2,6-(Cl)₂ | A + B | ++ | ++++ | ++++ | 0 | ++++ | 0 | 0 | ++ | ++ | ++ | 0 |
| 2,4-(Cl)₂ | 4-OCH₃ | A + B | ++++ | ++++ | ++++ | + | ++++ | ++ | 0 | 0 | ++++ | ++ | + |
| 2,4-(Cl)₂ | 4-Cl | | ++++ | ++++ | ++++ | + | ++++ | ++ | ++ | ++ | ++ | ++++ | + |
| 2,4-(Cl)₂ | H | | ++++ | ++++ | ++++ | + | ++++ | ++ | + | ++ | ++++ | ++++ | + |

Table B

ACTIVITY AGAINST PHYCOMYCETES.

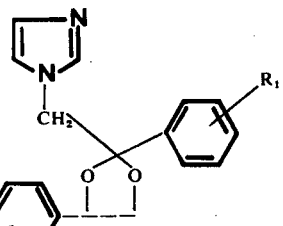

| R₁ | R₂ | Abs.r. | Bas.m. | Mort. | Rhi. |
|---|---|---|---|---|---|
| 2,4-(Cl)₂ | 4-Cl | ++ | ++ | + | ++ |
| 4-Br | 2-Cl | + | + | + | ++ |
| 4-Br | 4-Br | +++ | ++ | ++ | ++ |
| 4-CH₃ | 4-Cl | ++ | ++ | + | + |
| 2,4-(Cl)₂ | 4-Br | +++ | ++ | ++ | ++ |
| 4-Cl | 4-Br | +++ | ++ | ++ | ++ |
| 2-Cl | 4-Br | ++ | ++ | + | ++ |
| 4-Br | 4-CH₃ | ++ | ++ | + | ++ |
| 4-Cl | 4-F | ++ | ++ | + | + |
| 4-Br | 4-F | ++ | ++ | + | ++ |

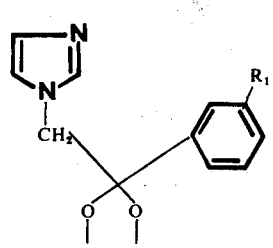

Table B-continued

ACTIVITY AGAINST PHYCOMYCETES.

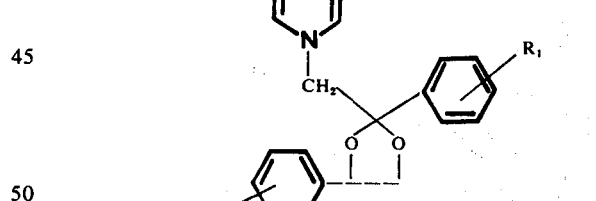

| R₁ | R₂ | Isomer | Abs.r. | Bas.m. | Mort. | Rhi. |
|---|---|---|---|---|---|---|
| 4-Cl | 4-Cl | B | +++ | + | + | + |
| 4-Cl | 4-F | cis | ++ | + | + | + |
| 4-Cl | 2-CH₃ | A | ++ | ++ | + | + |
| 4-Cl | 2,4-(Cl)₂ | B | +++ | ++ | ++ | + |
| 2,4-(Cl)₂ | 2-CH₃ | A | + | + | + | + |
| 2,4-(Cl)₂ | 4-Cl | trans | ++ | + | ++ | + |
| 2,4-(Cl)₂ | 2-CH₃,4-Cl | A + B | ++ | ++ | + | + |
| 4-Cl | 2,6-(Cl)₂ | A | ++ | + | + | + |
| 2,4-(Cl)₂ | 2-CH₃ | A | ++ | ++ | + | + |
| 2,4-(Cl)₂ | 4-CH₃ | A | + | ++ | + | + |
| 2,4-(Cl)₂ | 4-OCH₃ | A | ++ | ++ | + | + |
| 2,4-(Cl)₂ | 4-Cl | cis | ++ | ++ | + | + |
| 2,4-(Cl)₂ | 4-Br | A | +++ | ++ | ++ | ++ |
| 2,4-(Cl)₂ | H | A | ++ | ++ | + | + |
| 2,4-(Cl)₂ | 3,4-(Cl)₂ | A | +++ | +++ | + | ++ |
| 2,4-(Cl)₂ | 3-Cl | A | ++ | +++ | ++ | ++ |
| 2,4-(Cl)₂ | 2-Cl | A | +++ | ++ | + | + |

Table B-continued
ACTIVITY AGAINST PHYCOMYCTES.

| | | | | | | |
|---|---|---|---|---|---|---|
| 2,4-(Cl)₂ | 2-Br | cis | ++ | ++ | + | + |

Table C 1
BACTERIOSTATIC AND BACTERIOCIDAL ACTIVITY

All compounds were inactive against the gram-negative bacteria: Salmonella pull. gall., Escherichia coli and Pseudomonas aerug. The table summarizes the activity against the gram-positive bacteria.

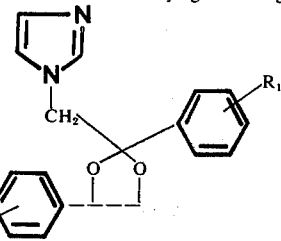

| R₁ | R₂ | bacteriostatic activity | | | bacteriocidal activity | | |
|---|---|---|---|---|---|---|---|
| | | E.ins. | Staph. | Strept. | E.ins. | Staph. | Strept. |
| 4-Cl | 4-Cl | ++ | ++ | ++ | ++ | ++ | ++ |
| 4-Cl | H | ++ | ++ | +++ | ++ | + | +++ |
| 4-Cl | 2,4-(Cl)₂ | +++ | ++ | +++ | ++ | ++ | +++ |
| 4-Br | 4-Cl | +++ | +++ | +++ | +++ | + | +++ |
| 4-Br | 2,4-(Cl)₂ | +++ | + | +++ | +++ | + | +++ |
| 2,4-(Cl)₂ | H | ++ | 0 | ++ | ++ | 0 | ++ |
| 4-OCH₃ | 4-Cl | ++ | + | ++ | + | + | ++ |
| H | 2,4-(Cl)₂ | ++ | ++ | +++ | + | + | ++ |
| 2,4-(Cl)₂ | 4-Cl | +++ | ++ | +++ | ++ | + | ++ |
| H | 4-Cl | +++ | + | +++ | + | + | ++ |
| 4-Cl | 2-Cl | +++ | ++ | +++ | ++ | + | ++ |
| 2-Cl | 2,4-(Cl)₂ | +++ | ++ | +++ | ++ | + | +++ |
| 4-Br | 2-Cl | +++ | + | ++ | +++ | + | ++ |
| 2-Cl | 4-Cl | +++ | + | +++ | +++ | + | +++ |
| 2,4-(Cl)₂ | 2,4-(Cl)₂ | +++ | ++ | +++ | +++ | + | +++ |
| 4-Br | H | ++ | + | +++ | ++ | + | +++ |
| H | 4-Br | +++ | 0 | +++ | +++ | 0 | +++ |
| 4-CH₃ | 2,4-(Cl)₂ | +++ | +++ | +++ | +++ | ++ | +++ |
| 4-Br | 4-Br | +++ | ++ | +++ | +++ | + | +++ |
| 2,4-(Cl)₂ | 2-Cl | +++ | +++ | +++ | +++ | ++ | +++ |
| 4-CH₃ | 4-Cl | +++ | ++ | +++ | +++ | + | +++ |
| 2,4-(Cl)₂ | 4-Br | +++ | ++ | +++ | ++ | + | ++ |
| 4-Cl | 4-Br | +++ | ++ | +++ | +++ | ++ | +++ |
| 4-CH₃ | 4-Br | +++ | ++ | +++ | +++ | + | +++ |
| 3-Cl | 2,4-(Cl)₂ | ++ | + | +++ | ++ | + | +++ |
| 2-Cl | 4-Br | ++ | ++ | ++ | ++ | + | ++ |
| 4-CH₃ | 2-Cl | +++ | + | +++ | ++ | + | +++ |
| 4-Cl | 4-CH₃ | +++ | + | +++ | ++ | + | +++ |
| 4-Br | 4-CH₃ | +++ | ++ | ++ | ++ | + | ++ |
| 4-Cl | 4-F | + | 0 | ++ | + | 0 | ++ |
| 4-Br | 4-F | ++ | + | +++ | ++ | + | +++ |

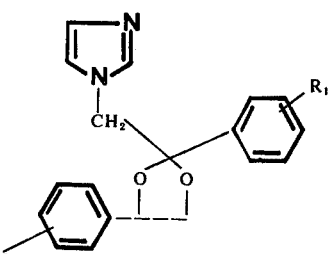

| R₁ | R₂ | Abs.r. | Bas.m. | Mort. | Rhi. |
|---|---|---|---|---|---|

Table C 2
BACTERIOSTATIC AND BACTERIOCIDAL ACTIVITY

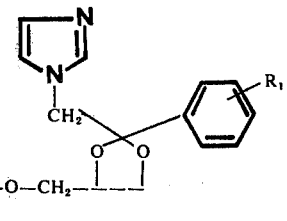

| R₁ | R₂ | Isomer | bacteriostatic activity | | | bacteriocidal activity | | |
|---|---|---|---|---|---|---|---|---|
| | | | E.ins. | Staph. | Strept. | E.ins. | Staph. | Strept. |
| 4-Cl | 2-CH₃,4-Cl | cis | ++++ | 0 | ++++ | ++++ | 0 | ++++ |
| 4-Cl | 4-CH₃ | trans | +++ | ++ | +++ | +++ | + | +++ |
| 4-Cl | 2-CH₃,4-Cl | trans | ++++ | ++ | ++++ | ++++ | + | +++ |
| 4-Cl | 4-CH₃ | cis | +++ | ++ | +++ | +++ | + | +++ |
| 4-Cl | 4-Cl | A | ++++ | + | +++ | ++++ | + | +++ |
| 4-Cl | 4-Cl | B | ++++ | ++ | +++ | ++++ | + | +++ |

Table C 2-continued

BACTERIOSTATIC AND BACTERIOCIDAL ACTIVITY

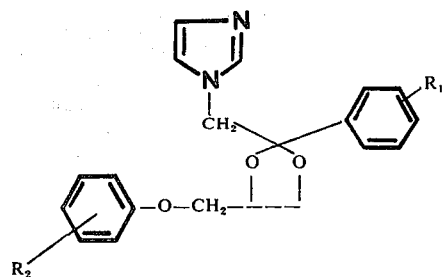

| $R_1$ | $R_2$ | Isomer | bacteriostatic activity | | | bacteriocidal activity | | |
|---|---|---|---|---|---|---|---|---|
| | | | E.ins. | Staph. | Strept. | E.ins. | Staph. | Strept. |
| 4-Cl | 2,4-(Cl)$_2$ | A | 0 | 0 | ++ | 0 | 0 | ++ |
| 4-Cl | 4-F | cis | +++ | 0 | +++ | +++ | 0 | +++ |
| 4-Cl | 2-CH$_3$ | A | ++++ | ++ | ++++ | ++++ | + | ++++ |
| 4-Cl | 2-Cl | A | +++ | 0 | +++ | +++ | 0 | +++ |
| 4-Cl | 2-CH$_3$ | B | ++++ | ++ | +++ | +++ | + | +++ |
| 4-Cl | 2,4-(Cl)$_2$ | B | ++++ | ++ | ++++ | ++++ | ++ | ++++ |
| 4-Cl | 4-OCH$_3$ | A | +++ | 0 | +++ | ++ | 0 | +++ |
| 4-Cl | 4-F | trans | ++ | + | ++ | + | + | ++ |
| 4-Cl | 4-OCH$_3$ | B | ++ | + | ++ | + | + | ++ |
| 4-Cl | 2,6-(Cl)$_2$ | A | +++ | 0 | ++++ | ++ | 0 | ++++ |
| 4-Cl | 2-Cl | B | +++ | + | ++ | +++ | + | ++ |
| 4-Cl | 2,6-(Cl)$_2$ | B | +++ | ++ | +++ | +++ | + | +++ |
| 2,4-(Cl)$_2$ | 4-CH$_3$ | B | ++ | ++ | ++ | ++ | + | ++ |
| 2,4-(Cl)$_2$ | 4-F | A | ++ | ++ | ++ | ++ | 0 | ++ |
| 2,4-(Cl)$_2$ | 2-CH$_3$ | A | +++ | + | +++ | +++ | + | +++ |
| 2,4-(Cl)$_2$ | 4-CH$_3$ | A | +++ | ++ | +++ | +++ | + | +++ |
| 2,4-(Cl)$_2$ | 4-OCH$_3$ | A | ++ | + | ++ | ++ | + | ++ |
| 2,4-(Cl)$_2$ | 4-Cl | cis | ++ | + | ++ | ++ | + | ++ |
| 2,4-(Cl)$_2$ | 2-CH$_3$ | B | +++ | + | +++ | +++ | + | +++ |
| 2,4-(Cl)$_2$ | 2,4-(Cl)$_2$ | A | +++ | 0 | +++ | +++ | 0 | +++ |
| 2,4-(Cl)$_2$ | 4-Cl | trans | +++ | ++ | +++ | +++ | ++ | +++ |
| 2,4-(Cl)$_2$ | 4-Br | A | +++ | + | +++ | +++ | + | +++ |
| 2,4-(Cl)$_2$ | 2,4-(Cl)$_2$ | B | +++ | ++ | +++ | ++ | + | +++ |
| 2,4-(Cl)$_2$ | H | A | +++ | + | +++ | +++ | + | +++ |
| 2,4-(Cl)$_2$ | 3,4-(Cl)$_2$ | A | +++ | ++ | +++ | +++ | + | +++ |
| 2,4-(Cl)$_2$ | 3-Cl | A | +++ | ++ | +++ | +++ | ++ | +++ |
| 2,4-(Cl)$_2$ | 2-Cl | A | +++ | ++ | +++ | +++ | + | +++ |
| 2,4-(Cl)$_2$ | 2-CH$_3$,4-Cl | A + B | +++ | ++ | +++ | ++ | + | +++ |
| 2,4-(Cl)$_2$ | 2-Cl | B | +++ | + | +++ | ++ | + | +++ |
| 2,4-(Cl)$_2$ | 2,6-(Cl)$_2$ | A | +++ | ++ | +++ | ++ | + | ++ |
| 2,4-(Cl)$_2$ | 3,5-(CH$_3$)$_2$,4-Cl | A | +++ | 0 | +++ | +++ | 0 | +++ |
| 2,4-(Cl)$_2$ | 2,4-(Br)$_2$ | A | +++ | 0 | +++ | +++ | 0 | +++ |
| 2,4-(Cl)$_2$ | 4-CN | A | +++ | + | ++ | 0 | 0 | ++ |
| 2,4-(Cl)$_2$ | 2-Br | cis | +++ | ++ | +++ | +++ | + | +++ |
| 2,4-(Cl)$_2$ | 2-OCH$_3$ | A | +++ | + | +++ | +++ | + | +++ |
| 2,4-(Cl)$_2$ | 2-Br | trans | +++ | ++ | ++ | +++ | + | ++ |
| 2,4-(Cl)$_2$ | 2,4,6-(Cl)$_3$ | A | +++ | 0 | +++ | ++ | 0 | ++ |
| 2,4-(Cl)$_2$ | 2,5-(CH$_3$)$_2$ | A | +++ | ++ | +++ | +++ | + | +++ |
| 2,4-(Cl)$_2$ | 2,5-(CH$_3$)$_2$ | B | +++ | ++ | +++ | +++ | + | +++ |
| 2,4-(Cl)$_2$ | 2-Cl,4-tert.but. | A | +++ | 0 | ++ | +++ | 0 | ++ |
| 2,4-(Cl)$_2$ | 2,4,5-(Cl)$_3$ | A | ++++ | 0 | ++ | +++ | 0 | ++ |
| 2,4-(Cl)$_2$ | 2-Cl,4-tert.but. | B | ++++ | ++ | ++++ | +++ | + | +++ |
| 2,4-(Cl)$_2$ | 2,4,5-(Cl)$_3$ | B | +++ | + | +++ | ++ | + | ++ |
| 2,4-(Cl)$_2$ | 2,5-(Br)$_2$,4-CH$_3$ | A | +++ | + | +++ | ++ | + | ++ |
| 2,4-(Cl)$_2$ | 2-F | A | +++ | + | ++++ | ++ | + | +++ |
| 4-CH$_3$ | 4-Br | A | +++ | ++ | ++++ | ++ | + | +++ |
| 4-Cl | 4-Br | A | ++++ | ++ | ++++ | +++ | + | +++ |
| 4-Br | 4-Br | A | ++++ | + | +++ | +++ | + | +++ |
| 2,4-(Cl)$_2$ | 2-OC$_2$H$_5$ | A | ++++ | 0 | ++++ | +++ | 0 | +++ |
| 2-Cl | 4-Br | A + B | ++++ | ++ | ++++ | +++ | + | +++ |
| 2-Cl | 4-Br | B | +++ | ++ | ++++ | ++ | + | +++ |
| H | 4-Br | A | +++ | ++ | ++++ | + | 0 | +++ |
| 2-Br | 4-Br | A | ++++ | +++ | ++++ | +++ | ++ | +++ |
| 2-Br | 4-Br | B | ++++ | ++ | ++++ | +++ | + | ++++ |
| 2,4-(Cl)$_2$ | 4-C$_6$H$_5$ | A + B | ++++ | 0 | ++ | +++ | 0 | ++ |
| 2,4-(Cl)$_2$ | 4-C$_6$H$_5$ | B | 0 | 0 | ++++ | 0 | 0 | +++ |
| 2,4-(Cl)$_2$ | 2,6-(CH$_3$)$_2$ | A | ++++ | ++ | ++++ | +++ | ++ | +++ |
| 2,4-(Cl)$_2$ | 4-Br | B | +++ | +++ | +++ | ++ | + | ++ |
| 2,4-(Cl)$_2$ | 2,6-(CH$_3$)$_2$ | A + B | +++ | ++ | +++ | ++ | + | ++ |
| 2,4-(Cl)$_2$ | 3,5-(CH$_3$)$_2$ | A | +++ | ++ | +++ | ++ | + | +++ |
| 2,4-(Cl)$_2$ | 4-iC$_3$H$_7$ | A + B | ++ | ++ | +++ | ++ | + | ++ |
| 2,4-(Cl)$_2$ | 2-Cl,6-CH$_3$ | A | ++ | ++ | ++ | ++ | + | ++ |
| 2,4-(Cl)$_2$ | 4-tert.but. | A | +++ | ++ | ++ | ++ | + | ++ |
| 2,4-(Cl)$_2$ | 3,5-(Cl)$_2$ | A | ++ | +++ | ++++ | ++ | ++ | +++ |
| 2,4-(Cl)$_2$ | 3-CH$_3$,4-Cl | A | +++ | ++ | ++ | ++ | ++ | + |

Table C 3

BACTERIOSTATIC AND BACTERIOCIDAL ACTIVITY

| $R_1$ | $R_2$ | Isomer | Bacteriostatic activity | | | Bacteriocidal activity | | |
|---|---|---|---|---|---|---|---|---|
| | | | E. ins. | Staph. | Strept. | E. ins. | Staph. | Strept. |
| 2,4-$(Cl)_2$ | 4-Br | A + B | +++ | ++ | ++++ | ++ | + | +++ |
| 2,4-$(Cl)_2$ | H | A + B | ++++ | ++ | ++++ | +++ | + | +++ |

Table C 4

| $R_1$ | $R_2$ | Isomer | Bacteriostatic activity | | | bacteriocidal activity | | |
|---|---|---|---|---|---|---|---|---|
| | | | E. ins. | Staph. | Strept. | E. ins. | Staph. | Strept. |
| 2,4-$(Cl)_2$ | 2-Cl | | +++ | +++ | ++++ | +++ | ++ | +++ |
| 2,4-$(Cl)_2$ | 2,4-$(Cl)_2$ | | ++++ | +++ | ++++ | +++ | ++ | +++ |
| 2,4-$(Cl)_2$ | 2,6-$(Cl)_2$ | A + B | ++++ | +++ | ++++ | +++ | ++ | +++ |
| 2,4-$(Cl)_2$ | 4-$OCH_3$ | A + B | ++++ | + | +++ | +++ | + | ++ |
| 2,4-$(Cl)_2$ | 4-Cl | | ++++ | ++ | ++++ | +++ | + | +++ |
| 2,4-$(Cl)_2$ | H | | ++++ | ++ | +++ | +++ | 0 | ++ |

The following examples are given to illustrate but not to limit the scope of the present invention. Unless otherwise stated all parts are by weight.

A. NOVEL INTERMEDIATES OF FORMULA III

EXAMPLE I

A mixture of 11.7 parts of 2-bromo-4'-chloroacetophenone, 9 parts of 1-(p-chlorophenyl)-1,2-ethanediol, 0.5 parts of p-toluenesulfonic acid and 80 parts of benzene is stirred and refluxed for 2 days with water-separator. The reaction mixture is cooled and washed successively twice with a sodium hydrogen carbonate solution and once with water. The organic phase is dried and evaporated. The residue is triturated in petroleum ether and cooled on ice. The precipitated product is filtered off, crystallized from methanol, stirred in acetonitrile while cooling on ice, filtered off again and washed once more with acetonitrile, yielding 2-(bromomethyl)-2,4-bis(-chlorophenyl)-1,3-dioxolane.

EXAMPLE II

A mixture of 11.6 parts of 2-bromo-4'-chloroacetophenone, 8.4 parts of α-hydroxymethyl)-benzylalcohol, 0.1 parts of p-toluene sulfonic acid, 210 parts of benzene and 40 parts of ethanol is stirred and refluxed for 24 hours. The reaction mixture is evaporated and the residue is triturated in methanol. The product is filtered off and crystallized from methanol, yielding 2-(bromomethyl)-2-(p-chlorophenyl)-4-phenyl-1,3-dioxolane; mp. 60°C.

EXAMPLE III

A mixture of 11.6 parts of 2-bromo-4'-chloroacetophenone, 12.4 parts of 1-(2.4-dichlorophenyl)-1,2-ethanediol, 0.1 parts of p-toluenesulfonic acid, 80 parts of n-butanol and 160 parts of benzene is stirred and refluxed for 24 hours with water-separator. The solvent is removed in vacuo and the residue is triturated in methanol. The precipitated product is filtered off and crystallized from petroleum ether, yielding 2-(bromoethyl)-2-(p-chlorophenyl)-4-(2,4-dichlorophenyl)-1,3-dioxolane; m.p. 82.7°C.

EXAMPLE IV

Following the procedure of Example III and using equivalent amounts of the appropriate starting materials, the following dioxolanes are prepared:

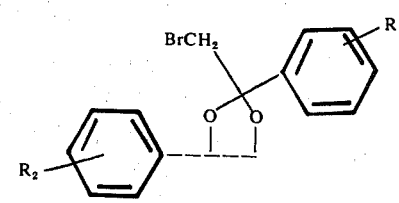

| $R_1$ | $R_2$ | Melting Point |
|---|---|---|
| 4-Br | 4-Cl | 101.3° |
| 4-Br | 2,4-$(Cl)_2$ | 99.9° |
| 4-$OCH_3$ | 4-Cl | 115.6° |
| — | 4-Cl | 63.9° |
| 4-$CH_3$ | 2,4-$(Cl)_2$ | 89.9° |

-continued

[Structure: dioxolane with BrCH₂, R₁-phenyl, R₂-phenyl substituents]

| R₁ | R₂ | Melting Point |
|---|---|---|
| 4-Br | 4-Br | 96.8° |
| 4-CH₃ | 4-Cl | 122° |
| 4-CH₃ | 4-Br | 118.6° |
| 4-CH₃ | 2-Cl | |

EXAMPLE V

A mixture of 13.4 parts of 2-bromo-2',4'-dichloroacetophenone, 8.4 parts of α-(hydroxymethyl)benzyl alcohol, 1.15 parts of p-toluenesulfonic acid, 160 parts of benzene and 140 parts of n-butanol is stirred and refluxed for 48 hours with a water-separator. The solvent is removed in vacuo. The residue is purified by column-chromatography over silica gel, using chloroform as eluent. The pure fractions are collected and the eluent is evaporated, yielding 2-(bromomethyl)-2-(2,4-dichlorophenyl)-4-phenyl-1,3-dioxolane as residue.

EXAMPLE VI

Following the procedure of Example V but substituting for the α-(hydroxymethyl)benzyl alcohol used therein equivalent amounts of 2,4-dichloro-α-(hydroxymethyl)benzyl alcohol and p-chloro-α-(hydroxymethyl)benzyl alcohol, and using the appropriately substituted 2-bromoacetophenone, there are prepared 2-(bromomethyl)-4-(2,4-dichlorophenyl)-2-phenyl-1,3-dioxolane and 2-(bromomethyl)-4-(p-chlorophenyl)-2-(2,4-dichlorophenyl)-1,3-dioxolane.

EXAMPLE VII

A mixture of 11.5 parts of 2-bromo-p-chloroacetophenone, 10.4 parts of o-chloro-α-(hydroxymethyl)benzylalcohol, 0.2 parts of p-toluenesulfonic acid, 180 parts of benzene and 80 parts of butanol is stirred and refluxed overnight with water-separator. The solvent is removed in vacuo and the residue is dissolved in chloroform. The chloroform solution is stirred with silica gel for 30 minutes. The silica gel is filtered off and the solvent is removed in vacuo, yielding 2-(bromomethyl)-4-(o-chlorophenyl)-2-(p-chlorophenyl)-1,3-dioxolane as a residue.

EXAMPLE VIII

Following the procedure of Example VII and using equivalent amounts of the appropriate starting materials, the following dioxolanes are prepared:

[Structure: dioxolane with BrCH₂, R₁-phenyl, R₂-phenyl substituents]

| R₁ | R₂ | Melting Point |
|---|---|---|
| 2-Cl | 2,4-(Cl)₂ | |
| 4-Br | 2-Cl | |
| 2-Cl | 4-Cl | |
| 2,4-(Cl)₂ | 2,4-(Cl)₂ | |
| 4-Br | — | 70° |
| — | 4-Br | 71.3° |
| 2,4-(Cl)₂ | 2-Cl | |
| 2,4-(Cl)₂ | 4-Br | |
| 4-Cl | 4-Br | 80.5° |
| 3-Cl | 2,4-(Cl)₂ | |
| 2-Cl | 4-Br | |
| 4-Cl | 4-CH₃ | |
| 4-Br | 4-CH₃ | |
| 4-Cl | 4-F | |
| 4-Br | 4-F | |

EXAMPLE IX

A mixture of 11.7 parts of 2-bromo-4'-chloroacetophenone, 11.9 parts of 1-(4-chloro-o-tolyloxy)-2,3-propanediol, 2.5 parts of p-toluenesulfonic acid and 240 parts of benzene is stirred and refluxed for 24 hours in a four-necked round-bottomed flask equipped with a watertrap. The benzene solution is washed successively with a diluted sodium hydroxide solution and with water. The solvent is removed in vacuo. The residue is crystallized from methanol and the less pure fraction is recrystallized from diisopropylether, yielding A-2-(bromomethyl-2-(p-chlorophenyl)-4-(4-chloro-o-tolyloxymethyl)-1,3-dioxolane; m.p. 102.5°C. The methanol filtrate is evaporated in vacuo, yielding B-2-(bromomethyl)-2-(p-chlorophenyl)-4-(4-chloro-o-tolyloxymethyl)-1,3-dioxolane as a residue.

EXAMPLE X

Following the procedure of Example IX and using equivalent amounts of the appropriate starting materials, the following dioxolanes are prepared:

[Structure: dioxolane with BrCH₂, R₁-phenyl, R₂-phenyl-O-CH₂- substituents]

| Isomer | R₁ | R₂ | Melting Point |
|---|---|---|---|
| A | 4-Cl | 4-CH₃ | |
| B | 4-Cl | 4-CH₃ | |
| A | 4-Cl | 2,4-Cl | |
| B | 4-Cl | 2,4-Cl | |
| A | 4-Cl | 4-F | 102° |
| B | 4-Cl | 4-F | |
| A | 4-Cl | 2-CH₃ | 82.2 – 85° |
| B | 4-Cl | 2-CH₃ | |
| A | 4-Cl | 2-Cl | 85 – 88.6° |
| B | 4-Cl | 2-Cl | |
| A | 4-Cl | 4-OCH₃ | |
| B | 4-Cl | 4-OCH₃ | |
| A | 2,4-(Cl)₂ | 4-F | |

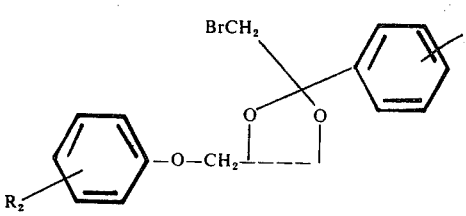

| Isomer | R₁ | R₂ | Melting Point |
|---|---|---|---|
| A | 2,4-(Cl)₂ | 4-OCH₃ | |

EXAMPLE XI

A mixture of 11.7 parts of 2-bromo-4′-chloroacetophenone, 12.2 parts of 1-(p-chlorophenoxy)-2,3-propanediol, 3 parts of p-toluenesulfonic acid and 240 parts of benzene is stirred and refluxed for 20 hours in a four-necked round-bottom flask equipped with a watertrap. The benzene solution is washed successively with a diluted sodium hydroxide solution and with water. The solvent is removed in vacuo. The residue is triturated in methanol. The precipitated product is filtered off (methanol filtrate is set aside) and crystallized from toluene, yielding A-2-(bromomethyl-4-(p-chlorophenoxymethyl)-2-(p-chlorophenyl)-1,3-dioxolane; m.p. 165°C.

The methanol filtrate is evaporated in vacuo. The residue is chromatographed over silica gel with chloroform as eluent, yielding B-2-(bromomethyl)-4-(p-chlorophenoxymethyl)-2-(p-chlorophenyl)-1,3-dioxolane as a residue.

EXAMPLE XII

A mixture of 13.4 parts of 2-bromo-2′, 4′-dichloroacetophenone, 11.2 parts of 1-(p-tolyloxy)-2,3-propanediol, 3 parts of p-toluenesulfonic acid and 240 parts of benzene is stirred and refluxed in a four-necked round-bottomed flask, equipped with a watertrap. When no more water is evolved (20 hours), the benzene solution is washed successively with diluted sodium hydroxide solution and twice with water. The solution is dried and the solvent is removed in vacuo. The residue is triturated in methanol. The precipitated product is filtered off (filtrate is set aside) and crystallized from butanol, yielding A-2-(bromomethyl)-2-(2,4-dichlorophenyl)-4-(p-tolyloxymethyl)-1,3-dioxolane.

The methanol filtrate (see above) is evaporated in vacuo and residue is dissolved in chloroform. This solution is stirred with silica gel for 5 hours. The mixture is filtered and the filtrate is evaporated in vacuo, yielding B-2-(bromomethyl)-2-(2,4-dichlorophenyl)-4-(p-tolyloxymethyl)-1,3-dioxolane.

EXAMPLE XIII

Following the procedure of Example XII and using equivalent amounts of the appropriate starting materials, the following dioxolanes are prepared:

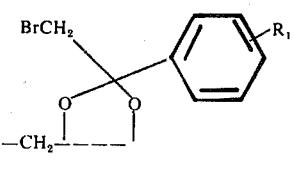

| Isomer | R₁ | R₂ | Melting Point |
|---|---|---|---|
| A | 2,4-(Cl)₂ | 4-Cl | |
| B | 2,4-(Cl)₂ | 4-Cl | |
| A | 2,4-(Cl)₂ | 2,4-(Cl)₂ | |
| B | 2,4-(Cl)₂ | 2,4-(Cl)₂ | |
| A | 2,4-(Cl)₂ | — | 97.6° |
| A | 2,4-(Cl)₂ | 3,4-(Cl)₂ | |
| A | 2,4-(Cl)₂ | 3-Cl | |
| A | 2,4-(Cl)₂ | 4-Cl,3,5-(CH₃)₂ | 115.8° |
| A | 2,4-(Cl)₂ | 2,4-(Br)₂ | |
| A | 2,4-(Cl)₂ | 4-CN | |
| A | 2,4-(Cl)₂ | 2-OCH₃ | |
| A+B | 2,4-(Cl)₂ | 4-C₆H₅ | |
| A+B | 2,4-(Cl)₂ | 4-iC₃H₇ | 90° |
| A | 2,4-(Cl)₂ | 4-Cl,3-CH₃ | |
| A | 2,4-(Cl)₂ | 3,5-(Cl)₂ | |
| A | 2,4-(Cl)₂ | 4-tert.butyl | |

EXAMPLE XIV

A mixture of 11.7 parts of 2-bromo-4′-chloroacetophenone, 14.2 parts of 1-(2,6-dichlorophenoxy)-2,3-propanediol, and 3 parts of p-toluenesulfonic acid and 240 parts of benzene is stirred and refluxed for 20 hours in a four-necked round-bottomed flask equipped with watertrap. The benzene-solution is washed successively with a diluted sodium hydroxide solution and with water. The solvent is removed in vacuo, yielding A + B-2-(bromomethyl)-2-(p-chlorophenyl)-4-(2,6-dichlorophenoxymethyl)-1,3-dioxolane as a residue.

EXAMPLE XV

A mixture of 13.4 parts of 2-bromo-2′,4′-dichloroacetophenone, 11.2 parts of 3-(o-tolyloxy)-1,2-propanediol, 3 parts of p-toluenesulfonic acid and 240 parts of benzene is stirred and refluxed in a four-necked round bottomed flask equipped with a watertrap. After 20 hours, the theoretical amount of water is evolved and the reaction mixture is allowed to cool to room temperature. The mixture is washed successively with diluted sodium hydroxide solution and twice with water. The solvent is removed in vacuo and the residue is dissolved in chloroform. This solution is stirred with silica gel, filtered and the filtrate is evaporated in vacuo, yielding A + B-2-(bromomethyl)-2-(2,4-dichlorophenyl)-4-(o-tolyloxymethyl)-1,3-dioxolane.

EXAMPLE XVI

Following the procedure of Example XV but substituting for the 3-(o-tolyloxy)-1,2-propanediol used therein equivalent amounts of the appropriate starting material, the following dioxolanes are prepared: A + B 2-(bromomethyl)-4-(o-chlorophenoxymethyl)-2-(2,4-dichlorophenyl)-1,3-dioxolane; 2-(bromomethyl)-4-(2,6-dichlorophenoxymethyl)-2-(2,4-dichlorophenyl)-1,3-dioxolane; A + B 2-(bromomethyl)-4-(o-bromophenoxymethyl)-2-(2,4-dichlorophenyl)-1,3-dioxolane; A + B 2-(bromomethyl)-4-(4-bromophenoxymethyl)-2-(2-bromophenyl)-1,3-dioxolane; A + B 2-(bromomethyl)-4-(2-chloro-6-methylphenoxymethyl)-

2-(2,4-dichlorophenyl)-1,3-dioxolane; and A + B 2-(bromomethyl)-4-(2,3-dichlorophenoxymethyl)-2-(2,4-dichlorophenyl)-1,3-dioxolane.

EXAMPLE XVII

A mixture of 6 parts of 2-bromo-2', 4'-dichloroacetophenone, 6 parts of 3-(4-chloro-o-tolyloxy)-1,2-propanediol, 3 parts of p-toluenesulfonic acid, 80 parts of n-butanol and 180 parts of benzene is stirred and refluxed for 24 hours with water-separator. The solvent is removed in vacuo and the residue is triturated in methanol. The product is filtered off and crystallized from petroleumether, yielding A +B 2-(bromomethyl)-4-(4-chloro-2-tolyloxymethyl)-2-(2,4-dichlorophenyl)-1,3-dioxolane.

EXAMPLE XVIII

A mixture of 13.6 parts of 2-bromo-1-(2,4-dichlorophenyl)-1-ethanone, 12 parts of 3-(2,5-dimethylphenoxy)-1,2-propanediol, 3 parts of 4-methylbenzenesulfonic acid, 80 parts of butanol and 180 parts of benzene is stirred and refluxed for 24 hours with water-separator. The reaction mixture is evaporated and the residue is dissolved in trichloromethane. The solution is stirred with silicagel for 30 minutes. The latter is filtered off and the filtrate is evaporated, yielding A + B 2-(bromomethyl)-2-(2,4-dichlorophenyl)-4-(2,5-dimethylphenoxymethyl)-1,3-dioxolane as a residue.

EXAMPLE XIX

Following the procedure of Example XVIII and using equivalent amounts of the appropriate starting materials, the following dioxolanes are prepared:

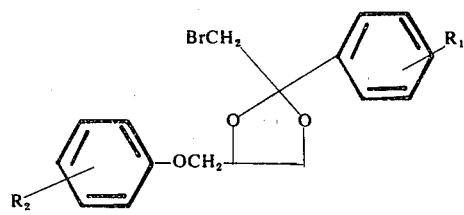

| Isomer | $R_1$ | $R_2$ |
|---|---|---|
| A+B | 2,4-$(Cl)_2$ | 2,4,6-$Cl_3$ |
| A+B | 2,4-$(Cl)_2$ | 2-Cl,4-$C(CH_3)_3$ |
| A+B | 2,4-$(Cl)_2$ | 2,4,5-$(Cl)_3$ |
| A+B | 2,4-$(Cl)_2$ | 2,5-$(Br)_2$,4-$CH_3$ |
| A+B | 2,4-$(Cl)_2$ | 2-$OC_2H_5$ |
| A+B | 2-Cl | 4-Br |

EXAMPLE XX

A mixture of 13.6 parts of 2-bromo-2',4'-dichloroacetophenone, 18 parts of 3-(6-bromo-2-napthyloxy)-1,2-propanediol, 3 parts of p-toluenesulfonic acid, 80 parts of n-butanol and 180 parts of benzene is stirred and refluxed for 24 hours with water-separator. The reaction mixture is evaporated. The residue is dissolved in chloroform and the solution is stirred with silica gel for one hour. The latter is filtered off and the filtrate is evaporated. The residue is crystallized twice: first from diisopropylether and then from dibutylether, yielding A 2-(bromomethyl)-4-(6-bromo-2-naphthyloxymethyl)-2-(2,4-dichlorophenyl)-1,3-dioxolane.

EXAMPLE XXI

A mixture of 13.6 parts of 2-bromo-1-(2,4-dichlorophenyl)-1-ethanone, 13.1 parts of 3-(2-naphtalenyloxy)-1,2-propanediol, 3 parts of 4-methylbenzenesulfonic acid, 180 parts of benzene and 80 parts of butanol is stirred and refluxed for 12 hours with water-separator. The reaction mixture is evaporated and the residue is triturated in methanol. The product is filtered off and crystallized from 2-propanol, yielding A 2-(bromomethyl)-2-(2,4-dichlorophenyl)-4-[(2-naphthalenyloxy)methyl]-1,3-dioxolane; mp. 117.6°C.

EXAMPLE XXII

Following the procedure of Example XXI and using equivalent amounts of the appropriate starting materials, the following dioxolanes are prepared:

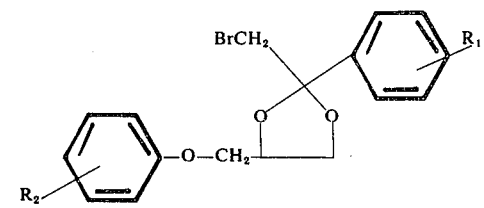

| Isomer | $R_1$ | $R_2$ | Melting Point |
|---|---|---|---|
| A | 2,4-$(Cl)_2$ | 2-F | 125.7° |
| A+B | 4-$CH_3$ | 4-Br | 121.1° |
| A+B | 4-Cl | 4-Br | 157.4° |
| A+B | 4-Br | 4-Br | 158.7° |
| A | 2,4-$(Cl)_2$ | 3-Br | 112.7° |
| A | 2,4-$(Cl)_2$ | 3,5-$(CH_3)_2$ | 118.7° |
| A+B | 2,4-$(Cl)_2$ | 4-$CH_2$-$C_6H_5$ | 106.1° |
| A+B | 4-$OCH_3$ | 4-Br | 117° |
| A | — | 4-Br | 85.6° |

EXAMPLE XXIII

A mixture of 13.6 parts of 2-bromo-1-(2,4-dichlorophenyl)-1-ethanone, 15.2 parts of 3-(4-chloro-1-naphthalenyloxy)-1,2-propanediol, 3 parts of 4-methylbenzenesulfonic acid, 80 parts of butanol and 180 parts of benzene is stirred and refluxed for 24 hours with water-separator. The reaction mixture is evaporated and the residue is triturated in 2-propanol. The product is filtered off and crystallized from butanol, yielding A + B 2-(bromomethyl)-4-(4-chloro-1-naphthalenyloxymethyl)-2-(2,4-dichlorophenyl)-1,3-dioxolane; mp. 122.7°C.

EXAMPLE XXIV

A mixture of 13.6 parts of 2-bromo-1-(2,4-dichlorophenyl)-1-ethanone, 15.8 parts of 3-(4-bromophenylthio)-1,2-propanediol, 3 parts of 4-methylbenzenesulfonic acid, 180 parts of butanol and 90 parts of benzene is stirred and refluxed for 12 hours with water-separator. The reaction mixture is evaporated and the residue is dissolved in trichloromethane. The solution is stirred with silica gel for 30 minutes. The latter is filtered off and the filtrate is evaporated, yielding A + B 2-(bromomethyl)-4-(4-bromophenylthiomethyl)-2-(2,4-dichlorophenyl)-1,3-dioxolane as a residue.

EXAMPLE XXV

A mixture of 13.6 parts of 2-bromo-1-(2,4-dichlorophenyl)-1-ethanone, 11.1 parts of 3-(phenylthio)-1,2-propanediol, 3 parts of 4-methylbenzenesulfonic acid, 80 parts of butanol and 180 parts of benzene is stirred and refluxed for 24 hours with water-separator. The reaction mixture is evaporated and the residue is dissolved in trichloromethane. The solution is stirred with silica gel for 30 minutes. The latter is filtered off and the filtrate is evaporated, yielding A + B 2-(bromomethyl)-2-(2,4-dichlorophenyl)-4-(phenylthiomethyl)-1,3-dioxolane as a residue.

EXAMPLE XXVI

A mixture of 222.5 parts of 2-bromo-1-(2,4-dichlorophenyl)-1-ethanone, 250 parts of 3-(4-bromophenoxy)-1,2-propanediol, 50 parts of 4-methylbenzenesulfonic acid and 3150 parts of benzene is stirred and refluxed in a four-necked, round-bottomed flask, equipped with a water-trap. After 16 hours the theoretical amount of water is evolved. The reaction mixture is allowed to cool to room temperature and washed successively with diluted sodium hydroxide solution and twice with water. The solvent is dried and removed in vacuo. The residue is triturated in methanol. The product is filtered off (the filtrate is set aside) and crystallized from butanol, yielding A-2-(bromomethyl)-4-(p-bromophenoxymethyl)-2-(2,4-dichlorophenyl)-1,3-dioxolane.

The filtrate (see above) is evaporated. The residue is dissolved in 210 parts of 2,2'-oxybispropane and the solution is allowed to crystallize. The precipitated product is filtered off and discarded. The filtrate is evaporated and the residue is dissolved in 400 parts of a mixture of hexane and trichloromethane (3 : 1 by volume). The undissolved part is filtered off and discarded. The filtrate is purified twice by column-chromatography over silica gel using a mixture of hexane and trichloromethane (3 : 1 by volume) as eluent. The pure fractions are collected and the eluent is evaporated. The residue solidifies on triturating in petroleumether. The product is filtered off and dried, yielding B-2-(bromomethyl)-4-(4-bromophenoxymethyl)-2-(2,4-dichlorophenyl)-1,3-dioxolane.

EXAMPLE XXVII

A mixture of 11.8 parts of 3-(2,6-dimethylphenoxy)-1,2-propanediol, 13.6 parts of 2-bromo-1-(2,4-dichlorophenyl)-1-ethanone, 3 parts of 4-methylbenzenesulfonic acid, 80 parts of butanol and 180 parts of methylbenzene is stirred and refluxed for 3 days. The reaction mixture is evaporated and the residue is dissolved in 2,2'-oxybispropane. The solution is stirred for 30 minutes with silica gel. The latter is filtered off and the filtrate is evaporated, yielding A + B 2-(bromomethyl)-2-(2,4-dichlorophenyl)-4-(2,6-dimethylphenoxymethyl)-1,3-dioxolane as a residue.

EXAMPLE XXVIII

A mixture of 11.2 parts of 2,2',4'-trichloroacetophenone, 14.9 parts of 1-(2,4-dichlorophenoxy)-2,3-propanediol, 3 parts of p-toluenesulfonic acid and 240 parts of benzene is stirred and refluxed for 20 hours in a four-necked, round-bottomed flask, equipped with a water-trap. The reaction mixture is washed successively with a diluted sodium hydroxide solution and twice with water. The solvent is removed in vacuo. The residue is triturated in methanol for 3 hours. The precipitated product is filtered off and crystallized from 2-propanol, yielding A-2-(chloromethyl)-4-(2,4-dichlorophenoxymethyl)-2-(2,4-dichlorophenyl)-1,3-dioxolane; mp. 92.5°C.

EXAMPLE XXIX

A mixture of 24 parts of 3-(4-bromophenoxy)-1,2-propanediol, 28 parts of 2-(bromomethyl)-2-(2,3,4-tri-chlorophenyl)-1,3-dioxolane, 4 parts of 4-methylbenzenesulfonic acid, 40 parts of butanol and 225 parts of methylbenzene is stirred and refluxed for 2 days. The reaction mixture is allowed to cool to room temperature and evaporated. The residue is triturated in methanol. The product is filtered off and crystallized from 2-propanol, yielding A-2-(bromomethyl)-4-(4-bromophenoxymethyl)-2-(2,3,4-trichlorophenyl)-1,3-dioxolane.

EXAMPLE XXX

A mixture of 14.4 parts of 1-[2-(4-methylphenyl)ethyl]-ethanediol, 15.6 parts of 2-(bromomethyl)-2-(2,4-dichlorophenyl)-1,3-dioxolane, 5 parts of 4-methylbenzenesulfonic acid, 225 parts of methylbenzene and 40 parts of butanol is stirred and refluxed for 3 days with water-separator. The reaction mixture is evaporated and the residue is dissolved in 2,2'-oxybispropane. The solution is stirred for 30 minutes with silica gel. The latter is filtered off and the filtrate is evaporated, yielding 2-(bromomethyl-2-(2,4-dichlorophenyl)-4-[2-(4-methylphenyl)ethyl]-1,3-dioxolane as a residue.

EXAMPLE XXXI

To a stirred and refluxing Grignard-complex, previously prepared starting from 98 parts of 1-(chloromethyl)-2,4-dichlorobenzene and 14 parts of magnesium in 70 parts of 1,1-oxybisethane, is added dropwise a solution of 46.5 parts of 2-(chloromethyl)oxirane in 350 parts of 1,1'-oxybisethane. Upon completion, stirring at reflux temperature is continued overnight. The reaction mixture is cooled in an ice-bath and decomposed by dropwise addition of 120 parts of a concentrated hydrochloric acid solution. The whole is poured onto water and the layers are separated. The organic phase is washed three times with water. The aqueous phase is extracted with 1,1'-oxybisethane. The combined organic phases are dried, filtered and evaporated. The residue is distilled, yielding 2,4-dichloro-α-(chloromethyl)benzenepropanol; bp. 130°C. at 0.04 mm. pressure.

EXAMPLE XXXII

Following the procedure of Example XXXI and using equivalent amounts of the appropriate starting materials, the following compounds are prepared:

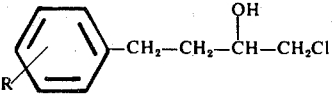

| R | boiling point |
|---|---|
| 2-Cl | 118°C. at 0.01 mm. pressure |
| 2,6-(Cl)$_2$ | 136°C. at 0.2 mm. pressure |
| 4-OCH$_3$ | 140°C. at 0.2 mm. pressure |
| 4-Cl | 130–135°C. at 0.3 mm. pressure |

EXAMPLE XXXIII

A solution of 87 parts of 2,4-dichloro-α-(chloromethyl)-benzenepropanol in 144 parts of concentrated sodium hydroxide solution and 350 parts of 2,2'- oxybispropane is stirred overnight at room temperature. The product is extracted with 2,2'-oxybispropane. The extract is washed with water, dried, filtered and evaporated. The oily residue is distilled, yielding [2-(2,4-dichlorophenyl)ethyl]oxirane; bp. 90°–98°C. at 0.01 mm. pressure.

EXAMPLE XXXIV

Following the procedure of Example XXXIII and using equivalent amounts of the appropriate starting materials, the following oxirane derivatives are prepared:

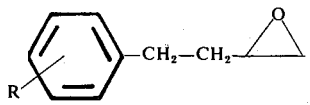

| R | boiling point |
|---|---|
| 2-Cl | 66–70°C. at 0.01 mm. pressure |
| 2,6-(Cl)₂ | 85–89°C. at 0.01 mm. pressure |
| 4-OCH₃ | 80–90°C. at 0.05 mm. pressure |
| 4-Cl | 106–115°C. at 0.03 mm. pressure |

EXAMPLE XXXV

A mixture of 50 parts of [2-(2,4-dichlorophenyl)ethyl]-oxirane, 7 parts of ethanedioic acid, 300 parts of 1,4-dioxane and 150 parts of water is stirred and refluxed for 36 hours. The reaction mixture is evaporated. The residue is crystallized from 2,2'-oxybispropane. The product is filtered off and dried at the air, yielding 1-[2-(2,4-dichlorophenyl)ethyl]ethanediol; mp. 83.2°C.

EXAMPLE XXXVI

By repeating the procedure of Example XXXV and using therein an equivalent amount of the appropriate starting material, the following compounds are prepared:

1-[2-(2-chlorophenyl)ethyl]ethanediol; mp. 64.1°C.;
4-(2,6-dichlorophenyl)-1,2-butanediol; mp. 111.7°C.; and
1-[2-(4-chlorophenyl)ethyl]ethanediol; bp. 150°C. at 0.02 mm. pressure.

EXAMPLE XXXVII

To a stirred solution of 12 parts of 2-[2-(4-methoxyphenyl)-ethyl]oxirane in 1.8 parts of sulfuric acid and 160 parts of 2-propanone are added 100 parts of water. The whole is stirred for 2 days at room temperature. The reaction mixture is stirred with a sodium bicarbonate solution and the product is extracted with trichloromethane. The extract is dried, filtered and evaporated, yielding 1-[2-(4-methoxyphenyl)ethyl]-1,2-ethanediol as a residue.

EXAMPLE XXXVIII

A mixture of 13.6 parts of 2-bromo-1-(2,4-dichlorophenyl)-1-ethanone, 14.1 parts of 1-[2-(2,4-dichlorophenyl)ethyl]ethanediol, 3 parts of 4-methylbenzenesulfonic acid, 80 parts of butanol and 180 parts of benzene is stirred and refluxed for 24 hours. The reaction mixture is evaporated and the residue is stirred for 2 hours with 160 parts of methanol. The precipitated product is filtered off, yielding 2-(bromomethyl)-2-(2,4-dichlorophenyl)-4-[2-(2,4-dichlorophenyl)ethyl]-1,3-dioxolane.

EXAMPLE XXXIX

Following the procedure of Example XXXVIII and using an equivalent amount of the appropriate starting material, the following dioxolanes are prepared:
2-(bromomethyl)-4-[2-(2-chlorophenyl)ethyl]-2-(2,4-dichlorophenyl)-1,3-dioxolane;
2-(bromomethyl)-2-(2,4-dichlorophenyl)-4-[2-(2,6-dichlorophenyl)ethyl]-1,3-dioxolane; and
A + B 2-(bromomethyl)-2-(2,4-dichlorophenyl)-4-[2-(4-methoxyphenyl)ethyl]-1,3-dioxolane.

EXAMPLE XL

A mixture of 11.2 parts of 1-[2-(4-chlorophenyl)ethyl]ethanediol, 15.6 parts of 2-(bromomethyl)-2-(2,4-dichlorophenyl)-1,3-dioxolane, 4 parts of 4-methylbenzenesulfonic acid, 40 parts of butanol and 225 parts of methylbenzene is stirred and refluxed for 5 days with water-separator. The reaction mixture is evaporated and the residue is dissolved in 2,2'-oxybispropane. The solution is stirred with silica gel. The latter is filtered off and the filtrate is evaporated, yielding 2-(bromomethyl)-4-[2-(4-chlorophenyl)ethyl]2-(2,4-dichlorophenyl)-1,3-dioxolane as a residue.

EXAMPLE XLI

Following the procedure of Example XL and using therein an equivalent amount of 4-phenyl-1,2-butanediol as a starting material, there is obtained: 2-(bromomethyl)-2-(2,4-dichlorophenyl)-4-(2-phenylethyl)-1,3-dioxolane as a residue.

B. FINAL PRODUCTS OF FORMULA I

EXAMPLE XLII

A mixture of 1.1 parts of imidazole, 1 part of 2-(bromomethyl)-2,4-bis(p-chlorophenyl)-1,3-dioxolane, 0.4 parts of potassium iodide and 20 parts of dimethylformamide is stirred and refluxed for 12 hours. Water is added and the product is extracted with ether. The extract is washed twice with water, dried, filtered and evaporated. The residue of 1-[2,4-bis(p-chlorophenyl)-1,3- dioxolan-2-ylmethyl]imidazole is converted into the nitrate salt. The crude salt is filtered off and crystallized from a mixture of 2-propanol and diisopropylether, yielding 1-[2,4-bis(p-chlorophenyl)-1,3-dioxolan-2-ylmethyl]imidazole nitrate; mp. 192.3°C.

EXAMPLE XLIII

A mixture of 7 parts of imidazole, 7.5 parts of 2-(bromomethyl)-2-(p-chlorophenyl)-4-phenyl-1,3-dioxolane, 2 parts of sodium iodide and 100 parts of dimethyl formamide is stirred and refluxed for 48 hours. The reaction mixture is allowed to cool to room temperature and is poured into water. The product is extracted twice with benzene. The extract is washed twice with water and the solvent is removed in vacuo. The residue of 1-[2-(p-chlorphenyl)-4-phenyl-1,3-dioxolan-2-ylmethyl]imidazole is converted into the nitrate salt in 4-methyl-2-pentanone and diisopropylether. The crude salt is filtered off and crystallized from 4-methyl-2-pentanone, yielding 1-[2-(p-chlorophenyl)-4-phenyl-1,3-dioxolan-2-ylmethyl]-imidazole nitrate; mp. 153.2°C.

EXAMPLE XLIV

Following the procedure of Example XLIII and using equivalent amounts of the appropriate starting materials, the following imidazoles and imidazole acid addition salts are prepared:

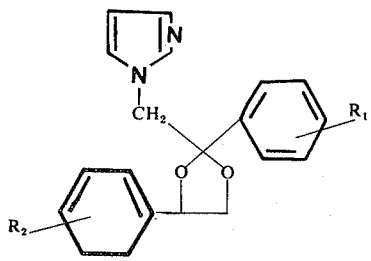

| $R_1$ | $R_2$ | Acid Salt | Melting Point of Salt |
|---|---|---|---|
| 4-Cl | 2,4-(Cl)$_2$ | HNO$_3$ | 196.6° |
| 4-Br | 4-Cl | HNO$_3$ | 152.6° |
| 4-Br | 2,4-(Cl)$_2$ | HNO$_3$ | 205.3° |
| 2,4-(Cl)$_2$ | — | 2(COOH)$_2$ | 107.7° |
| 4-OCH$_3$ | 4-Cl | HNO$_3$ | 196.3° |
| — | 2,4-(Cl)$_2$ | HNO$_3$ | 163.8° |
| 2,4-(Cl)$_2$ | 4-Cl | 1.5 (COOH)$_2$ | 119.9° |
| — | 4-Cl | HNO$_3$ | 134.7° |
| 4-Cl | 2-Cl | HNO$_3$ | 183.8° |
| 2-Cl | 2,4-(Cl)$_2$ | HNO$_3$ | 164.2° |
| 2,4-(Cl)$_2$ | 2-Cl | HNO$_3$ | 151° |

EXAMPLE XLV

A mixture of 13.6 parts of imidazole, 18.5 parts of 2-(bromomethyl)-2-(o-chlorophenyl)-4-(p-chlorophenyl)-1,3-dioxolane, 4 parts of sodium iodide and 150 parts of dimethyl formamide is stirred and refluxed for 72 hours. Water is added and the product is extracted twice with diisopropylether. The combined extracts are washed twice with water, dried, filtered, and evaporated. The residue is purified by column-chromatography over silica gel using chloroform as eluent. The pure fractions are collected and the eluent is evaporated. The residue of 1-[2-(o-chlorophenyl)-4-(p-chlorophenyl)-1,3-dioxolan-2-ylmethyl]imidazole is converted into the nitrate salt in 2-propanol and diisopropylether. The salt is filtered off and crystallized from a mixture of ethanol and diisopropylether, yielding 1-[2-(o-chlorophenyl)-4-(p-chlorophenyl)-1,3-dioxolan-2-ylmethyl]imidazole nitrate; mp. 183.1°C.

EXAMPLE XLVI

A mixture of 13.6 parts of imidazole, 18.6 parts of 2-(bromomethyl)-4-(p-bromophenyl)-2-(2,4-dichlorophenyl)-1,3-dioxolane, 4 parts of sodium iodide and 150 parts of dimethylformamide is stirred and refluxed for 3 days. The reaction mixture is poured into water and the product is extracted twice with diisopropylether. The combined extracts are washed twice with water, dried, filtered, and evaporated. The residue is purified by column-chromatography over silica gel using chloroform as eluent. The pure fractions are collected and the eluent is evaporated. The residue, 1-[4-(p -bromophenyl)-2-(2,4-dichlorophenyl)-1,3-dioxolan-2-ylmethyl]imidazole, is converted into the nitrate salt in 2-propanol and diisopropylether. The salt is filtered off and crystallized from a mixture of 2-propanol and diisopropylether, yielding 1-[4-(p-bromophenyl)-2-(2,4-dichlorophenyl)-1,3-dioxolan-2-ylmethyl]imidazole nitrate; mp. 141.9°C.

EXAMPLE XLVII

A mixture of 13.6 parts of imidazole, 17.5 parts of 2-(bromomethyl)-2-(p-bromophenyl)-4-(o-chlorophenyl)-1,3-dioxolane, 4 parts of sodium iodide and 150 parts of dimethyl formamide is stirred and refluxed for 3 days. Water is added and the product is extracted twice with diisopropylether. The combined extracts containing 1-[2-(p-bromophenyl)-4-(o-chlorophenyl)-1,3-dioxolane-2-ylmethyl]imidazole are washed twice with water and acidified with an excess of a concentrated nitric acid solution. The nitrate salt is filtered off and crystallized from a mixture of ethanol and diisopropylether, yielding 1-[2-(p -bromophenyl)-4-(o-chlorophenyl)-1,3-dioxolan-2-ylmethyl]imidazole nitrate; mp. 194.7°C.

EXAMPLE XLVIII

Following the procedure of Example XLVII and using equivalent amounts of the appropriate starting materials, the following imidazoles and imidazole acid addition salts are prepared:

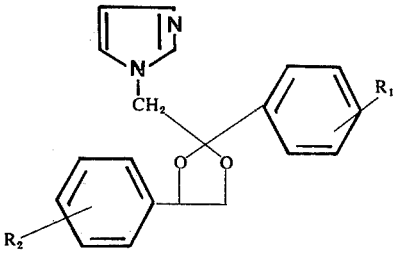

| $R_1$ | $R_2$ | Acid Salt | Melting Point of Salt |
|---|---|---|---|
| 2,4-(Cl)$_2$ | 2,4-(Cl)$_2$ | HNO$_3$ | 161.2° |
| 4-Br | — | HNO$_3$ | 156.5° |
| — | 4-Br | HNO$_3$ | 131.1° |
| 4-CH$_3$ | 2,4-(Cl)$_2$ | HNO$_3$ | 193.6° |
| 4-Br | 4-Br | HNO$_3$ | 144.3° |
| 4-CH$_3$ | 4-Cl | HNO$_3$ | 200.8° |
| 4-Cl | 4-Br | HNO$_3$ | 145.2° |
| 4-CH$_3$ | 4-Br | HNO$_3$ | 210.5° |
| 3-Cl | 2,4-(Cl)$_2$ | HNO$_3$ | 165.4° |
| 2-Cl | 4-Br | HNO$_3$ | 184.1° |
| 4-CH$_3$ | 2-Cl | HNO$_3$ | 207.5° |
| 4-Cl | 4-CH$_3$ | HNO$_3$ | 144.3° |
| 4-Br | 4-CH$_3$ | HNO$_3$ | 140.2° |
| 4-Cl | 4-F | HNO$_3$ | 163.2° |
| 4-Br | 4-F | HNO$_3$ | 179.3° |

EXAMPLE IL

To a stirred solution of 2.3 parts of sodium in 80 parts of methanol are added 6.8 parts of imidazole, followed by the addition of 100 parts of dimethyl formamide and the methanol is removed at atmospheric pressure till an internal temperature of 130°C is reached. Then there are added 7 parts A-2-(bromomethyl)-2-(p-chlorophenyl)-4-(4-chloro-o-tolyloxymethyl)-1,3-dioxolane and the mixture is stirred and refluxed for 3 hours. The reaction mixture is poured into water and the product is extracted with benzene. The extract is dried and evaporated in vacuo. The residue of A-1-[2-(p-chlorophenyl)-4-(4-chloro-o-tolyloxymethyl)-1,3-dioxolan-2-ylmethyl]imidazole is converted into the nitrate salt in 2-propanol. Upon the addition of diisopropylether, the salt is precipitated. It is filtered off and crystallized from a mixture of methanol and diisopropylether, yielding cis1-[2-(p-chlorophenyl)-4-(4-chloro-o-tolyloxymethyl)-1,3-dioxolan-2-ylmethyl]imidazole nitrate; mp. 164.3°C.

EXAMPLE L

Following the procedure of Example IL and using equivalent amounts of the appropriate starting materials, the following imidazoles and imidazole acid addition salts are prepared:

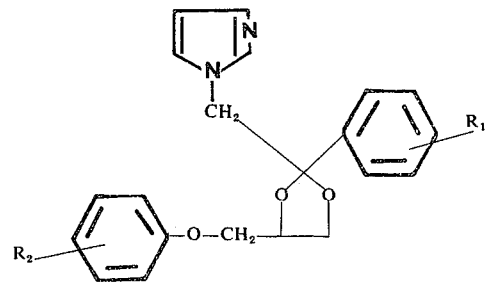

| Isomer | R₁ | R₂ | Acid Salt | Melting Point of Salt |
|---|---|---|---|---|
| trans | 4-Cl | 4-Cl,2-CH₃ | HNO₃ | 190 – 190.7° |
| cis | 4-Cl | 4-CH₃ | HNO₃ | 140.2° |
| trans | 4-Cl | 4-CH₃ | HNO₃ | 160° |
| trans | 4-Cl | 4-Cl | HNO₃ | 171.8 – 176.9° |
| cis | 4-Cl | 4-Cl | HNO₃ | 165.8 – 169.6° |
| B | 4-Cl | 2,4-Cl | HNO₃ | 160 – 165.3° |
| cis | 4-Cl | 4-F | HNO₃ | 172.3 – 174.5° |
| trans | 4-Cl | 4-F | HNO₃ | 175.9° |
| A | 4-Cl | 2-CH₃ | HNO₃ | 134.6 – 145.4° |
| B | 4-Cl | 2-CH₃ | HNO₃ | 156.6 – 161.6° |
| B | 4-Cl | 2-Cl | HNO₃ | 170.5° |
| B | 4-Cl | 4-OCH₃ | HNO₃ | 133.2° |

EXAMPLE LI

To a stirred solution of 2.3 parts of sodium in 80 parts of methanol are added 6.8 parts of imidazole, 150 parts of dimethylformamide and 2 parts of sodium iodide at room temperature. The methanol is removed at atmospheric pressue till an internal temperature of 130°C is reached. Then there are added 8 parts of A-2-(bromomethyl)-2-(p-chlorophenyl)-4-(2,4-dichlorophenoxymethyl)-1,3-dioxolane and the whole is stirred and refluxed for 2 hours. The reaction mixture is allowed to cool to room temperature and water is added (400 parts). The reaction mixture is diluted with 80 parts of diisopropylether, whereupon the product is crystallized. it is filtered off and recrystallized from 4-methyl-2-pentanone, yielding A-1-[2-(p-chlorophenyl)-4-(2,4-dichlorophenoxymethyl)-1,3-dioxolane-2-ylmethyl]imidazole; mp. 175.4°–179.5°C.

EXAMPLE LII

Following the procedure of Example LI but substituting for the A-2-(bromomethyl)-2-(p-chlorophenyl)-4-(2,4-dichlorophenoxymethyl)-1,3-dioxolane used therein equivalent amounts of A-2-(bromomethyl)-4-(o-chlorophenoxymethyl)-2-(p-chlorophenyl)-1,3-dioxolane and A-2-(bromomethyl)-2-(p-chlorophenyl)-4-(p-methoxyphenoxymethyl)-1,3-dioxolane there are prepared A-1-[4-(o-chlorophenoxymethyl)-2-(p-chlorophenyl)-1,3-dioxolan 2-ylmethyl]imidazole (mp. 140.8°–143.6 °) and A-1-[2-p-chlorophenyl)-4-(p-methoxyphenoxymethyl)-1,3-dioxolan-2-ylmethyl]imidazole (mp. 111.1°).

EXAMPLE LIII

To a stirred solution of 4.6 parts of sodium in 160 parts of methanol are added successively 13.6 parts of imidazole, 300 parts of dimethylformamide and 4 parts of sodium iodide. The methanol is distilled off at atmospheric pressure till an internal temperature of 130°C is reached. Then there are added 25.9 parts of A + B-2-(bromomethyl)-2-(p-chlorophenyl)-4-(2,6-dichlorophenoxymethyl)-1,3-dioxolane and the whole is stirred at reflux temperature for 2 hours. The reaction mixture is allowed to cool to room temperature and poured onto water. The product is extracted twice with benzene. The combined extracts are washed twice with water, dried and evaporated in vacuo. The residue, containing the A and B-isomers, is chromatographed over silica gel with chloroform as eluent. The A-isomer is collected as an oily free base and is converted into the nitrate salt in 2-propanol. The crude salt is crystallized from 2-propanol, yielding 3.8 parts of A-1-[2-(p-chlorophenyl)-4-(2,6-dichlorophenoxymethyl)-1,3-dioxolan-2-ylmethyl]imidazole nitrate; mp. 145.8°C. The B-isomer is also collected as an oily free base and is converted into the nitrate salt in 2-propanol and diisopropyl-ether. The crude salt is crystallized from 2-propanol, yielding 2.2 parts of B-1-[2-(p-chlorophenyl)-4-(2,6-dichlorophenoxymethyl)-1,3-dioxolan-2-ylmethyl]imidazole nitrate; mp. 197°–200.5°C.

EXAMPLE LIV

To a stirred solution of 4.6 parts of sodium in 120 parts of methanol are added successively 13.6 parts of imidazole, 200 parts of dimethylformamide and 2 parts of sodium iodide. The methanol is removed at atmospheric pressure, while stirring, till an internal temperature of 130°C is reached. Then there are added 21.5 parts of A + B-2-(bromomethyl)-2-(2,4-dichlorophenyl)-4-(o-tolyloxymethyl)-1,3-dioxolane and the whole is stirred and refluxed for 2 hours. The reaction mixture is allowed to cool to room temperature and poured onto water. The product is extracted with benzene (twice). The extracts are washed twice with water, dried, filtered and removed in vacuo. The residue is chromatographed over silica gel with chloroform as eluent. The A-isomer is collected and the eluent is evaporated. The free base residue is converted into the nitrate salt in 4-methyl-2-pentanone. Upon the addition of diisopropylether, the nitrate salt is precipitated. It is filtered off and crystallized from 4-methyl-2-pentanone, yielding A-1-[2-(2,4-dichlorophenyl)-4-(o-tolyloxymethyl)- 1,3-dioxolan-2-ylmethyl]imidazole nitrate.; mp. 156.2°C.

The B-isomer is collected too and the eluent is evaporated. The free base residue is converted into the oxalate salt in 4-methyl-2-pentanone and diisopropylether. The crude salt is filtered off and crystallized from 4-methyl-2-pentanone, yielding B -1-[2-(2,4-dichlorophenyl)-4-(o-tolyloxymethyl)-1,3-dioxolan-2-ylmethyl]imidazole sesquioxalate; mp. 138.5°C.

EXAMPLE LV

A mixture of 6.8 parts of imidazole, 8.5 parts of B -2-(bromomethyl)-4-(p-chlorophenoxymethyl)-2-(2,4-dichlorophenyl)-1,3-dioxolane, 2 parts of sodium iodide and 100 parts of dimethylformamide is stirred and refluxed for 36 hours. The reaction mixture is allowed to cool to room temperature and poured into water. The product is extracted twice with benzene. The combined organic layers are washed twice with water, dried and the solvent is removed in vacuo. The residue is purified by column-chromatography over silica gel using chloroform as eluent. The pure fractions are collected and the eluent is evaporated. The residue of B-1-[4-(p-chlorophenoxymethyl)-2-(2,4-dichlorophenyl)-1,3-dioxolan-2-ylmethyl]-imidazole is converted into the oxalate salt in 4-methyl-2-pentanone: upon the addition of diisopropylether, the salt is precipitated. It is filtered off and crystallized from 4-methyl-2-pentanone, yielding 3.1 parts of trans-1-[4-p-chlorophenoxymethyl)-2-(2,4-dichlorophenyl)-1,3-dioxolan-2-ylmethyl]-imidazole sesquioxalate; mp. 101°C.

EXAMPLE LVI

A mixture of 6.8 parts of imidazole, 8.9 parts of B-2-(bromomethyl)-4-(2,4-dichlorophenoxymethyl)-2-(2,4-dichlorophenyl)-1,3-dioxolane, 3 parts of sodium iodide and 100 parts of dimethyl formamide is stirred and refluxed for 48 hours. The reaction mixture is allowed to cool to room temperature and poured into water. The product is extracted twice with benzene. The combined extracts are washed twice with water and the solvent is removed in vacuo. The residue is purified by column-chromatography over silica gel, using chloroform as eluent. The pure fractions are collected and the eluent is evaporated. The residue of B-1-[4-(2,4-dichlorophenoxymethyl)-2-(2,4-dichlorophenyl)-1,3-dioxolan-2-ylmethyl]imidazole is converted into the oxalate salt in 4-methyl-2-pentanone: upon the addition of diisopropylether, the salt is precipitated. It is filtered off and crystallized twice from 4-methyl-2-pentanone, yielding B-1-[4-(2,4-dichlorophenoxymethyl)-2-(2,4-dichlorophenyl)-1,3-dioxolan-2-ylmethyl]-imidazole sesquioxalate; mp. 121.2°C.

EXAMPLE LVII

A mixture of 6.8 parts of imidazole, 7.8 parts of A-2-(bromomethyl)-2-(2,4-dichlorophenyl)-4-(phenoxymethyl)-1,3-dioxolane, 4 parts of sodium iodide and 150 parts of dimethylformamide is stirred and refluxed for 3 days. The reaction mixture is allowed to cool to room temperature, poured into water and the product is extracted twice with diisopropylether. The combined extracts containing A-1-[2-(2,4-dichlorophenyl)-4-(phenoxymethyl)-1,3-dioxolan-2-ylmethyl]imidazole are washed twice with water and acidified with an excess of a concentrated nitric acid solution. The salt is filtered off and crystallized from a mixture of ethanol and diisopropylether, yielding 5.6 parts of A-1-[2-(2,4-dichlorophenyl)-4-(phenoxymethyl)-1,3-dioxolan-2-ylmethyl]imidazole nitrate; mp. 180.5°C.

EXAMPLE LVIII

Following the procedure of Example LVII and using equivalent amounts of the appropriate starting materials, the following imidazoles and imidazole acid addition salts are prepared:

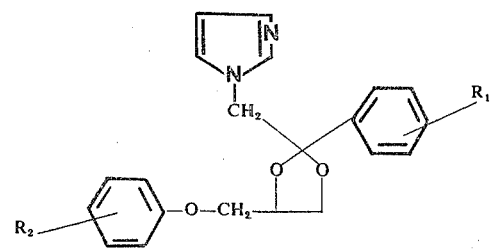

| Isomer | R₁ | R₂ | Acid Salt | Melting Point Of Salt |
|---|---|---|---|---|
| A | 2,4-(Cl)₂ | 3,4-(Cl)₂ | HNO₃ | 152.1° |
| A | 2,4-(Cl)₂ | 3-Cl | HNO₃ | 120.9° |
| A+B | 2,4-(Cl)₂ | 4-Cl,2-CH₃ | HNO₃ | 121.9° |
| A | 2,4-(Cl)₂ | 2,4-(Br)₂ | HNO₃ | 164.9° |
| A | 2,4-(Cl)₂ | 2-F | HNO₃ | 135.6° |
| A | H | 4-Br | HNO₃ | 167.6° |
| B | 2,4-(Cl)₂ | 4-Br | HNO₃ | 131.1° |

EXAMPLE LIX

A mixture of 6.8 parts of imidazole, 5 parts of A-2-(bromomethyl)-2-(2,4-dichlorophenyl)-4-(p-fluorophenoxymethyl)-1,3-dioxolane, 2 parts of sodium iodide and 50 parts of dimethylformamide is stirred and refluxed for 24 hours. The reaction mixture is allowed to cool to room temperature and then poured into water. The product is extracted twice with benzene. The combined organic phases are washed twice with water, dried, filtered, and evaporated in vacuo. The residue of A-1-[2-(2,4-dichlorophenyl)-4-(p-fluorophenoxymethyl)-1,3-dioxolan-2-ylmethyl]imidazole is converted into the nitrate salt in 2-propanol. The crude salt is filtered off and crystallized from 2-propanol, yielding 3.2 parts of A-1-[2-(2,4-dichlorophenyl)-4-(p-fluorophenoxymethyl)-1,3-dioxolan-2-ylmethyl]imidazole nitrate; mp. 151°–152°C.

EXAMPLE LX

Following the procedure of Example LIX and using equivalent amounts of the appropriate starting materials, the following imidazoles and imidazole acid addition salts are prepared:

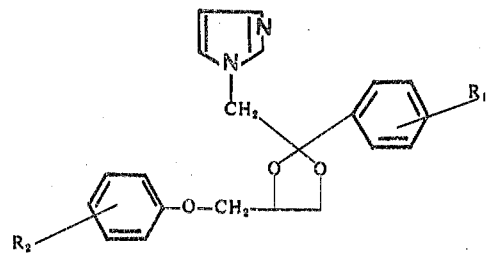

| Isomer | R₁ | R₂ | Acid Salt | Melting Point of Salt |
|---|---|---|---|---|
| A | 2,4-(Cl)₂ | 4-CH₃ | HNO₃ | 141.8° |
| B | 2,4-(Cl)₂ | 4-CH₃ | (COOH)₂ | 145.1° |
| A | 2,4-(Cl)₂ | 4-OCH₃ | (COOH)₂ | 184.7° |
| cis | 2,4-(Cl)₂ | 4-Cl | HNO₃ | 152.7° |
| A | 2,4-(Cl)₂ | 2,4-(Cl)₂ | HNO₃ | 146.5° |
| A | 2,4-(Cl)₂ | 4-Br | HNO₃ | 158.9° |
| A | 2,4-(Cl)₂ | 4-Cl,3,5-CH₃ | HNO₃ | 185.7° |
| A | 2,4-(Cl)₂ | 4-CN | HNO₃ | 208° |
| A | 2,4-(Cl)₂ | 2-OCH₃ | 2(COOH)₂ | 110.6° |

EXAMPLE LXI

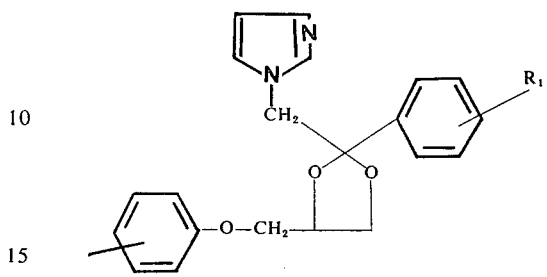

| Isomer | R₁ | R₂ | Acid Salt | Melting Point of Salt |
|---|---|---|---|---|
| A | 2,4—(Cl)₂ | 2,6—(Cl)₂ | HNO₃ | 159° |
| cis | 2,4—(Cl)₂ | 2—Br | HNO₃ | 142.2° |
| trans | 2,4—(Cl)₂ | 2—Br | 2(COOH)₂ | 151.3° |
| A | 2,4—(Cl)₂ | 2,5—(CH₃)₂ | HNO₃ | 180.9° |
| B | 2,4—(Cl)₂ | 2,5—(CH₃)₂ | 1.5(COOH)₂ | 142.7° |
| A | 2,4—(Cl)₂ | 2,4,6—(Cl)₃ | HNO₃ | 181.6° |
| B | 2,4—(Cl)₂ | 2,4,6—(Cl)₃ | 2(COOH)₂ | 143.9° |
| A | 2,4—(Cl)₂ | 2—Cl,4—C(CH₃)₃ | HNO₃ | 141.2° |
| B | 2,4—(Cl)₂ | 2—Cl,4—C(CH₃)₃ | HNO₃ | 141.1° |
| A | 2,4—(Cl)₂ | 2,4,5—(Cl)₃ | HNO₃ | 196.1° |
| B | 2,4—(Cl)₂ | 2,4,5—(Cl)₃ | 1.5(COOH)₂ | 173.6° |
| A | 2,4—(Cl)₂ | 2,5—(Br)₂,4—CH₃ | HNO₃ | 175.4° |
| A | 2,4—(Cl)₂ | 2OC₂H₅ | HNO₃ | 117.7° |
| A+B | 2—Cl | 4—Br | HNO₃ | 145.3° |
| B | 2—Cl | 4—Br | HNO₃ | 152.7° |
| A | 2—Br | 4—Br | HNO₃ | 149.9° |
| B | 2—Br | 4—Br | HNO₃ | 169.3° |
| A | 2,4—(Cl)₂ | 2—Cl,6—CH 3 | HNO₃ | 154.2° |

A mixture of 13.6 parts of imidazole, 22.2 parts of A + B-2-(bromomethyl)-4-(o-chlorophenoxymethyl)-2-(2,4-dichlorophenyl)-1,3-dioxolane, 4 parts of potassium iodide, and 150 parts of dimethylformamide is stirred and refluxed for 3 days. The reaction mixture is allowed to cool to room temperature, poured into water and the product is extracted twice with diisopropylether. The combined extracts are washed twice with water, dried, filtered and evaporated. The residue is purified by column-chromatography over silica gel using chloroform as eluent, yielding two fractions.

The first fraction is evaporated and the residue of A-1-[4-(o-chlorophenoxymethyl)-2-(2,4-dichlorophenyl)-1,3-dioxolan-2-ylmethyl]imidazole is dissolved in a mixture of 4-methyl-2-pentanone and diisopropylether. The solution is acidified with an excess of a concentrated nitric acid solutuion. The nitrate salt is filtered off and crystallized from a mixture of 4-methyl-2-pentanone and diisopropylether, yielding A-1-[4-(o-chlorophenoxymethyl)-2-(2,4-dichlorophenyl)-1,3-dioxolan-2-ylmethyl]imidazole nitrate; mp. 136.2°C.

The second fraction is evaporated and the residue of B-1-[4-(o-chlorophenoxymethyl)-2-(2,4-dichlorophenyl)-1,3-dioxolan-2-ylmethyl]imidazole is dissolved in a mixture of 4-methyl-2-pentanone and diisopropylether. The solution is acidified with an excess of oxalic acid. The oxalate salt is filtered off and crystallized from 4-methyl-2-pentanone, yielding 4parts of B-1-[4-(o-chlorophenoxymethyl)-2-(2,4-dichlorophenyl)-1,3-dioxolan-2-ylmethyl]imidazole dioxalate; mp. 103.5°C

EXAMPLE LXII

Following the procedure of Example LXI and using equivalent amounts of the appropriate starting materials, the following imidazoles and imidazole acid addition salts are prepared. Where only one isomer is listed, no second fraction was obtained from chromatography.

EXAMPLE LXIII

A mixture of 13.6 parts of imidazole, 12 parts of A 2-(bromomethyl)-4-(6-bromo-2-naphthyloxymethyl)-2-(2,4-dichlorophenyl)-1,3-dioxolane, 4 parts of potassium iodide and 150 parts of dimethylformamide is stirred and refluxed for 3 days. The reaction mixture is allowed to cool to room temperature, poured into water and the product is extracted twice with benzene. The combined extracts are washed twice with water, dried, filtered and evaporated. The residue of A-1-[4-(6-bromo-2-naphthyloxymethyl)-2-(2,4-dichlorophenyl)-1,3-dioxolan-2-ylmethyl]imidazole is converted into the nitrate salt in 4-methyl-2-pentanone and diisopropylether. The salt is filtered off and crystallized from a mixture of methanol and diisopropylether, yielding A 1-[4-(6-bromo-2-naphtyloxymethyl)-2-(2,4-dichlorophenyl)-1,3-dioxolan-2-ylmethyl]imidazole nitrate; mp. 195.5°C.

EXAMPLE LXIV

A mixture of 6.8 parts of 1H-imidazole, 6 parts of A 2-(bromomethyl)-2-(2,4-dichlorophenyl)-4-[(2-naphthalenyloxy)methyl]-1,3-dioxolane, 4 parts of potassium iodide and 150 parts of N,N-dimethylformamide is stirred and refluxed for 3 days. The reaction mixture is poured into water and the product is extracted twice with 1,1'-oxybisethane. The combined extracts containing A-1-[2-(2,4-dichlorophenyl)-4-(2-naphthalenyloxymethyl)-1,3-dioxolan-2-ylmethyl]-1H-imidazole are washed twice with water and acidified with an excess of a concentrated nitric acid solution. The nitrate salt is filtered off and crystallized from a mixture of ethanol and 2,2'-oxybispropane, yielding A-1-[2-(2,4-dichlorophenyl)-4-(2-naphthalenyloxymethyl)-1,3-dioxolan-2-ylmethyl]-1H-imidazole nitrate; mp. 156.3°C.

EXAMPLE LXV

A mixture of 9.7 parts of 1H-imidazole, 12.5 parts of A + B 2-(bromomethyl)-4-(4-bromophenoxymethyl)-2-(4-methylphenyl)-1,3-dioxolane, 3 parts of potassium iodide and 135 parts of N,N-dimethylformamide is stirred and refluxed for 72 hours. The reaction mixture is poured into water and the product is extracted twice with 1,1'-oxybisethane. The extract containing A-1-[4-(4-bromophenoxymethyl)-2-(4-methylphenyl)-1,3-dioxolan-2-ylmethyl]-1H-imidazole is washed twice with water, and an excess of a concentrated nitric acid solution and 2,2'-oxybispropane are added. The formed salt is filtered off and crystallized from a mixture of ethanol and 2,2'-oxybispropane, yielding 5.6 parts of A 1-[4-(4-bromophenoxymethyl)-2-(4-methylphenyl)-1,3-dioxolan-2-ylmethyl]-1H-imidazole nitrate; mp. 175.5°C.

EXAMPLE LXVI

Following the procedure of Example LXV but substituting for the A+B-2-(bromomethyl)-4-(4-bromophenoxymethyl)-2-(4-methylphenyl)-1,3-dioxolane used therein equivalent amounts of A+B-2-(bromomethyl)-4-(4-bromophenoxymethyl)-2-(4-chlorophenyl)-1,3-dioxolane and A+B-2-(bromomethyl)-4-(4-bromophenoxymethyl)-2-(4-bromophenyl)-1,3-dioxolane there are prepared A-1-[4-(4-bromophenoxymethyl)-2-(4-chlorophenyl)-1,3-dioxolan2-ylmethyl]-1H-imidazole and its nitrate salt (mp. 158°) and A-1-[4-(4-bromophenoxymethyl)-2-(4-bromophenyl)-1,3-dioxolan2-ylmethyl]-1H-imidazole and its nitrate salt (mp. 170.8°).

EXAMPLE LXVII

A mixture of 20.8 parts of 1H-imidazole, 21 parts of A + B 2-(bromomethyl)-4-(4-chloro-1-naphtalenyloxymethyl)-2-(2,4-dichlorophenyl)-1,3-dioxolane, 4 parts of potassium iodide and 135 parts of N,N-dimethylformamide is stirred and refluxed for 3 days. The reaction mixture is poured into water and the product is extracted twice with 2,2'-oxybispropane. The combined extracts containing A + B 1-[4-(4-chloro-1-naphthalenyloxymethyl)-2-(2,4-dichlorophenyl)-1,3-dioxolan-2-ylmethyl]-1H-imidazole are washed twice with water and an excess of a concentrated nitric acid solution is added. The nitrate salt is filtered off and crystallized from a mixture of ethanol and 2,2'-oxybispropane, yielding A + B 1-[4-(4-chloro-1-napthalenyloxymethyl)-2-(2,4-dichlorophenyl)-1,3-dioxolan-2-ylmethyl]-1H-imidazole nitrate; mp. 136.7°C.

EXAMPLE LXVIII

A mixture of 20.4 parts of 1H-imidazole, 27.2 parts of A + B 2-(bromomethyl)-4-(4-bromophenylthiomethyl)-2(2,4-dichlorophenyl)-1,3-dioxolane, 4 parts of potassium iodide and 180 parts of N,N-dimethylformamide is stirred and refluxed for 3 days. The reaction mixturue is poured into water and the product is extracted twice with 1,1'-oxybisethane. The combined extracts are washed twice with water, dried, filtered and evaporated. The residue is purified by column-chromatography over silica gel using trichloromethane as eluent. The pure fractions are collected and the eluent is evaporated. The residue of A + B-1-[4-(4-bromophenylthiomethyl)-2-(2,4-dichlorophenyl)-1,3-dioxolan-2-ylmethyl]-1H-imidazole is converted into the nitrate salt in 4-methyl-2-pentanone and 2,2'-oxybispropane. The salt is filtered off and crystallized from a mixture of ethanol and 2,2'-oxybispropane. The product is filtered off and dried, yielding A + B 1-[4-(4-bromophenylthiomethyl)-2-(2,4-dichlorphenyl)-1,3-dioxolan-2-ylmethyl]-1H-imidazole nitrate; mp. 170.0°C.

EXAMPLE LXIX

A mixture of 20.4 parts of 1H-imidazole, 20.5 parts of A + B 2-(bromomethyl)-2-(2,4-dichlorphenyl)-4-(phenylthiomethyl)-1,3-dioxolane, 4 parts of potassium iodide and 135 parts of N,N-dimethylformamide is stirred and refluxed for 3 days. The reaction mixture is poured into water and the product is extracted twice with 1,1'-oxybisethane. The combined extracts are washed twice with water, dried, filtered and evaporated. The residue is purified by column-chromatography over silica gel using trichloromethane as eluent. The pure fractions are collected and the eluent is evaporated. The residue of A + B 1-[2-(2,4-dichlorophenyl)-4-(phenylthiomethyl)-1,3-dioxolane-2-ylmethyl]-1H-imidazole is converted into the nitrate salt in 4-methyl2-pentanone and 2,2'-oxybispropane. The salt is filtered off and crystallized from a mixture of ethanol and 2,2'-oxybispropane. The product is filtered off and dried, yielding A + B 1-[2-(2,4-dichlorophenyl)-4-(phenylthiomethyl)-1,3-dioxolane-2-ylmethyl]-1H-imidazole nitrate; mp. 122.3° C.

EXAMPLE LXX

A mixture of 7.9 parts of 1H-imidazole, 11.5 parts of A + B 2-(bromomethyl)-2-(2,4-dichlorophenyl)-4-(4-phenylphenoxymethyl)-1,3-dioxolane, 4 parts of potassium iodide and 135 parts of N,N-dimethylformamide is stirred and refluxed for 3 days. The reaction mixture is poured onto water and the product is extracted twice with 1,1'-oxybisethane. The combined extracts are washed with water, dried, filtered and evaporated. The residue is purified by column-chromatography over silica gel, using trichloromethane as eluent.

The first fraction is collected and the eluent is evaporated. The rsidue is converted into the nitrate salt in 4-methyl-2-pentanone and 2,2'-oxybispropane. The salt is filtered off and crystallized from a mixture of ethanol and 2,2'-oxybispropane, yielding A + B 1-[2-(2,4-dichlorophenyl)-4-(4-phenylphenoxymethyl)-1,3-dioxolan-2-ylmethyl]-1H-imidazole nitrate; mp. 187.9°C.

The second fraction is collected and the eluent is evaporated. The residue is crystallized from 4-methyl-2-pentanone, yielding B 1-[2-(2,4-dichlorophenyl)-4-(4-phenylphenoxymethyl)-1,3-dioxolan-2-ylmethyl]-1H-imidazole; mp. 155.7°C.

EXAMPLE LXXI

To a stirred sodium methoxide solution, prepared starting from 2.3 parts of sodium in 48 parts of methanol, is added a mixture of 6.8 parts of 1H-imidazole and 180 parts of N,N-dimethylformamide. The methanol is distilled off at normal pressure till an internal temperature of 125°C. is reached. Then there are added 22.8 parts of A + B 2-(bromomethyl)-2-(2,4-dichlorophenyl)-4-(2,6-dimethylphenoxymethyl)-1,3-dioxolane and 3 parts of potassium iodide. The whole is stirred and refluxed for 24 hours. The reaction mixture is poured onto water and the product is extracted three times with 1,1'-oxybisethane. The combined extracts are washed twice with water, dried, filtered and evaporated. The residue is purified by column-chromatography over silica gel using trichloromethane as eluent.

The first fraction (A-isomer) is collected and the eluent is evaporated. The residue is converted into the nitrate salt in 4-methyl-2-pentanone and 2,2'-oxybispropane. The salt is filtered off and crystallized from a mixture of ethanol and 2,2'-oxybispropane, yielding A-1-[2-(2,4-dichlorophenyl)-4-(2,6-dimethylphenoxymethyl)-1,3-dioxolan-2-ylmethyl]-1H-imidazole nitrate; mp. 155.6°C.

The second fraction (B-isomer) is collected and the eluent is evaporated. The residue is converted into the nitrate salt in 4-methyl-2-pentanone and 2,2'-oxybispropane. The salt is filtered off and crystallized from a mixture of 2-propanol and 2,2'-oxybispropane, yielding A + B 1-[2-(2,4-dichlorophenyl)-4-(2,6-dimethylphenoxymethyl)-1,3-dioxolan-2-ylmethyl]-1H-imidazole nitrate; mp. 134.5°C.

EXAMPLE LXXII

A mixture of 8.6 parts of 1H-imidazole, 11.3 parts of A-2-(bromomethyl)-2-(2,4-dichlorophenyl)-4-(3,5-dimethylphenoxymethyl)-1,3-dioxolane, 4 parts of potassium iodide and 135 parts of N,N-dimethylacetamide is stirred and refluxed for 3 days. The reaction mixture is poured onto water and the product is extracted twice with 2,2'-oxybispropane. The combined extracts are washed twice with water and an excess of a concentrated nitric acid solution is added. The formed nitrate salt is filtered off and crystallized from a mixture of 2-propanol and 2,2'-oxybispropane. The product is filtered off again and recrystallized from 4-methyl-2-pentanone, yielding A-1-[2-(2,4-dichlorophenyl)-4-(3,5-dimethylphenoxymethyl)-1,3-dioxolan-2-ylmethyl]-1H-imidazole nitrate hydrate; mp. 122.6°C.

EXAMPLE LXXIII

A mixture of 5.4 parts of 1H-imidazole, 7.5 parts of A + B-2-(bromomethyl)-2-(2,4-dichlorophenyl)-4-[4-(1-methylethyl)-phenoxymethyl]-1,3-dioxolane, 3 parts of potassium iodide and 135 parts of N,N-dimethylacetamide is stirred and refluxed for 3 days. The reaction mixture is allowed to cool to room temperature, poured onto water and the product is extracted twice with 2,2'-oxybispropane. The combined extracts are washed twice with water and an excess of a concentrated nitric acid solution is added. The formed nitrate salt is filtered off and crystallized from a mixture of 2-propanol and 2,2'-oxybispropane, yielding A + B-1- 2-(2,4-dichlorophenyl)-4-[4-(1-methylethyl)phenoxymethyl]-1,3-dioxolan-2-ylmethyl -1H-imidazole nitrate.

EXAMPLE LXXIV

Following the procedure of Example LXXIII and using equivalent amounts of the appropriate starting materials, the following imidazoles and imidazole acid addition salts were prepared:
A-1- 2-(2,4-dichlorophenyl)-4-[4-(1,1-dimethylethyl)phenoxymethyl]-1,3-dioxolan-2-ylmethyl -1H-imidazole nitrate; mp. 169.5°C.;
A-1-[4-(3,5-dichlorophenoxymethyl)-2-(2,4-dichlorophenyl)-1,3-dioxolan-2-ylmethyl]-1H-imidazole nitrate hydrate; mp. 136.7°C.; and A-1-[4-(4-chloro-3-methylphenoxymethyl)-2-(2,4-dichlorophenyl)-1,3-dioxolan-2-ylmethyl]-1H-imidazole nitrate; mp. 142.8°C.

EXAMPLE LXXV

A mixture of 6.8 parts of 1H-imidazole, 8 parts of A-2-(bromomethyl)-4-(p-bromophenoxymethyl)-2-(2,4-dichlorophenyl)-1,3-dioxolane, 3 parts of sodium iodide and 90 parts of N,N-dimethylformamide is stirred and refluxed for 3 days. The reaction mixture is cooled and poured onto 500 parts of water. The product is extracted twice with 180 parts of methylbenzene. The combined extracts are washed twice with 200 parts of water, dried, filtered and evaporated. The residue is taken up in a mixture of methanol and 2,2'-oxybispropane, treated with activated charcoal and evaporated. The residue is converted into the nitrate salt in 4-methyl-2-pentanone. The salt is sucked off and the free base is liberated in the conventional manner. It is extracted with methylbenzene and the extract is dried, filtered and evaporated. The residue is triturated in 2,2'-oxybispropane. The product is filtered off and dried, yielding cis-1-[4-(4-bromophenoxymethyl)-2-(2,4-dichlorophenyl)-1,3-dioxolan-2-ylmethyl]-1H-imidazole; mp. 121.8°C.

EXAMPLE LXXVI

Following the procedure of Example LXXV and using equivalent amounts of the appropriate starting materials, the following imidazoles and imidazole acid additions salts are prepared:
1- 4-[2-(2-chlorophenyl)ethyl]-2-(2,4-dichlorophenyl)-1,3-dioxolan-2-ylmethyl -1H-imidazole nitrate; mp. 98.8°C.;
1- 2-(2,4-dichlorophenyl)-4-[2-(2,4-dichlorophenyl)ethyl]-1,3-dioxolan-2-ylmethyl -1H-imidazole nitrate; mp. 158.1°C.; and
A + B 1- 2-(2,4-dichlorophenyl)-4-[2-(2,6-dichlorophenyl)ethyl]-1,3-dioxolan-2-ylmethyl -1H-imidazole nitrate; mp. 140.1°C.

EXAMPLE LXXVII

A mixture of 14.4 parts of 1H-imidazole, 18.5 parts of A + B 2-(bromomethyl)-2-(2,4-dichlorophenyl)-4-[2-(4-methoxyphenyl)ethyl]-1,3-dioxolane, 5 parts of potassium iodide and 135 parts of N,N-dimethylacetamide is stirred and refluxed for 2 days. The reaction mixture is allowed to cool to room temperature and poured onto water. The product is extracted twice with 2,2'-oxybispropane. The combined extracts are washed with water, dried, filtered and evaporated. The residue is converted into the ethanedioate salt in 4-methyl-2-pentanone and 2,2'-oxybixpropane. The salt is filtered off and crystallized from a mixture of 2,2'-oxybispropane and ethanol, yielding A + B 1- 2-(2,4-dichlorophenyl)-4-[2-(4-methoxyphenyl)ethyl]-1,3-dioxolan-2-ylmethyl -1H-imidazole sesquiethanedioate; mp. 130.7°C.

EXAMPLE LXXVIII

Following the procedure of Example LXXVII and using equivalent amounts of the appropriate starting materials, the following imidazoles and imidazole acid addition salts are prepared:
1- 4-[2-(4-chlorophenyl)ethyl]-2-(2,4-dichlorophenyl)-1,3-dioxolan-2-ylmethyl -1H-imidazole diethanedioate; mp. 131.9°C.;
1-[2-(2,4-dichlorophenyl)-4-(2-phenylethyl)-1,3-dioxolan-2-yl-methyl]-1H-imidazole sesquiethanedioate; mp. 117.8°C.; and A + B 1- 2-(2,4-dichlorophenyl)-4-[2-(4-methylphenyl)ethyl]-1,3-dioxolan-2ylmethyl -1H-imidazole sesquiethanedioate hydrate; mp. 123.8°C.

EXAMPLE LXXIX

A mixture of 10.6 parts of 1H-imidazole, 15.8 parts of A-2-(bromomethyl)-4-(4-bromophenoxymethyl)-2-(2,3,4-trichlorophenyl)-1,3-dioxolane, 3 parts of potassium iodide and 135 parts of N,N-dimethylacetamide is stirred and refluxed for 2 days. The reaction mixture is allowed to cool to room temperature and poured onto water. The product is extracted twice with 1,1'-oxybisethane. The combined extracts are washed twice with water and acidified with an excess of a concentrated nitric acid solution. Upon the addition of 2,2'-oxybispropane, the formed nitrate salt is precipitated. it is filtered off and crystallized from a mixture of ethanol and 2,2'-oxybispropane, yielding A-1-[4-(4-bromophenoxymethyl)-2-(2,3,4-trichlorophenyl)-1,3-dioxolan-2-ylmethyl]-1H-imidazole nitrate; mp. 174.4°C.

EXAMPLE LXXX

A mixture of 17 parts of 1H-imidazole, 33.5 parts of A + B-2-(bromomethyl)-4-(2,3-dichlorophenoxymethyl)-2-(2,4-dichlorophenyl)-1,3-dioxolane, 3 parts of potassium iodide and 135 parts of N,N-dimethylacetamide is stirred and refluxed for 2 days. The reaction mixture is allowed to cool to room temperature and poured onto water. The product is extracted twice with 1,1'-oxybisethane. The combined extracts are washed twice with water, dried, filtered and evaporated. The residue is purified by columnchromatography over silica gel, using trichloromethane as eluent.

The first fraction (A-isomer) is collected and the eluent is evaporated. The residue is converted into the ethanedioate salt in 4-methyl-2-pentanone and 2,2'-oxybispropane. The salt is filtered off and crystallized from 4-methyl-2-pentanone, yielding A-1-[4-(2,3-dichlorophenoxymethyl)-2-(2,4-dichlorophenyl)-1,3-dioxolan-2ylmethyl -1H-imidazole diethanedioate; mp. 151.1°C.

The second fraction (B-isomer) is collected and the eluent is evaporated. The residue is converted into the ethanedioate salt in 4-methyl-2-pentanone and 2,2'-oxybispropane. The salt is filtered off and crystallized from 4-methyl-2-pentanone, yielding B-1-[4-(2,3-dichlorophenoxymethyl)-2-(2,4-dichlorophenyl)-1,3-dioxolan-2-ylmethyl]-1H-imidazole sesquiethanedioate; mp. 156.3°C.

What is claimed is:

1. A chemical compound selected from the group consisting of an imidazole derivative having the formula:

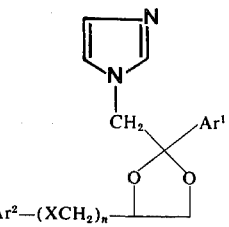

and the therapeutically active acid addition salts and stereochemical optical isomeric forms thereof, wherein:

$Ar^1$ is a member selected from the group consisting of phenyl, mono-, di- and trihalophenyl, loweralkylphenyl and loweralkoxyphenyl;

$Ar^2$ is a member selected from the group consisting of phenyl, substituted phenyl, naphthyl and halonaphthyl, and wherein substituted phenyl has the meaning of a phenyl group, having thereon from 1 to 3 substituents, independently selected from the group consisting of halo, loweralkyl, loweralkoxy, cyano, phenyl and benzyl;

X is a member selected from the group consisting of ·O, S and $CH_2$; and $n$ is the integer 0 or 1.

2. A chemical compound selected from the group consisting of A-1-[2-(2,4-dichlorophenyl)-4-(p-fluorophenoxymethyl)-1,3-dioxolan-2-ylmethyl]imidazole and the therapeutically acceptable acid addition salts thereof.

3. A chemical compound selected from the group consisting of A-1-[4-(p-bromophenoxymethyl)-2-(2,4-dichlorophenyl)-1,3-dioxolan-2-ylmethyl]imidazole and the therapeutically acceptable acid addition salts thereof.

4. A chemical compound selected from the group consisting of A-1-[2-(2,4-dichlorophenyl)-4-(p-methoxyphenoxymethyl)-1,3-dioxolan-2-ylmethyl-]imidazole and the therapeutically acceptable acid addition salts thereof.

5. A chemical compound selected from the group consisting of A-1-[2-(2,4-dichlorophenyl)-4-(2-fluorophenoxymethyl)-1,3-dioxolan-2-ylmethyl]-1H-imidazole and the therapeutically acceptable acid addition salts thereof.

6. A chemical compound selected from the group consisting of A-1-[4-(4-bromophenoxymethyl)-2-(4-chlorophenyl)-1,3-dioxolan-2-ylmethyl]-1H-imidazole and the therapeutically acceptable acid addition salts thereof.

* * * * *